United States Patent [19]

Nüsslein et al.

[11] 4,281,121
[45] Jul. 28, 1981

[54] 1,3,4-THIADIAZOLE-2-CARBOXYLIC ACID DERIVATIVES, PROCESS FOR MAKING THE SAME AND FUNGICIDAL AND NEMATOCIDAL COMPOSITIONS CONTAINING SAME

[75] Inventors: Ludwig Nüsslein; Dietrich Baumert; Ernst A. Pieroh, all of Berlin, Fed. Rep. of Germany

[73] Assignee: Schering Aktiengesellschaft, Berlin, Fed. Rep. of Germany

[21] Appl. No.: 101,061

[22] Filed: Dec. 6, 1979

[30] Foreign Application Priority Data

Dec. 7, 1978 [DE] Fed. Rep. of Germany ....... 2853196

[51] Int. Cl.$^3$ ................. C07D 285/12; C07D 417/06
[52] U.S. Cl. ............................. 544/134; 424/248.51; 424/267; 424/270; 546/209; 548/136; 560/148
[58] Field of Search ................... 548/136; 544/134; 546/209

[56] References Cited

FOREIGN PATENT DOCUMENTS 2253863 5/1974 Fed. Rep. of Germany ........... 548/136
2612761 10/1976 Fed. Rep. of Germany ........... 548/136

Primary Examiner—Alton D. Rollins
Attorney, Agent, or Firm—Michael J. Striker

[57] ABSTRACT

1,3,4-thiadiazole-2-carboxylic acid derivatives of the formula

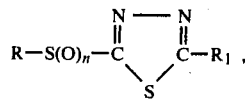

wherein R is $C_1$–$C_6$-alkyl, $C_2$–$C_6$-alkenyl, $C_2$–$C_6$-alkinyl or $C_3$–$C_6$-cycloalkyl, $R_1$ is $C_1$–$C_6$-alkoxycarbonyl, aminocarbonyl, $C_1$–$C_8$-alkylaminocarbonyl, $C_3$–$C_6$-cycloalkylaminocarbonyl, di-$C_1$–$C_8$ alkylaminocarbonyl, cyclohexylmethylaminocarbonyl, alkoxyalkylaminocarbonyl, morpholinocarbonyl, pyrrolidinocarbonyl, piperidinocarbonyl or cyano, and n is 0,1 or 2.

The compounds wherein n is 1 or 2 have both a high fungicidal and nematocidal activity. The compounds in which n is 0 are the starting products or intermediate products in making the compound in which a sulfonyl or sulfinyl group is present (n=1 or 2) but have also nematocidal properties of their own. All compounds of the invention avoid the undesirable environmental properties and other shortcomings of the prior art products, particularly those of the broadly used mercury compounds.

182 Claims, No Drawings

1,3,4-THIADIAZOLE-2-CARBOXYLIC ACID DERIVATIVES, PROCESS FOR MAKING THE SAME AND FUNGICIDAL AND NEMATOCIDAL COMPOSITIONS CONTAINING SAME

BACKGROUND OF THE INVENTION

The invention relates to 1,3,4-thiadiazole-2-carboxylic acid derivatives.

Compounds for use against phytopathogenic fungi are already known. Compounds in use of this kind are for instance manganeseethylene-bisdithiocarbamate (U.S. Pat. No. 2,504,404), N-trichloromethylmercaptotetrahydro-phthalimide and N-trichloromethylmercapto-phthalimide (U.S. Pat. No. 2,553,770, U.S. Pat. No. 2,553,771, U.S. Pat. No. 2,553,776), tetrachloroisophthalodinitrile (U.S. Pat. No. 3,290,353, U.S. Pat. No. 3,331,735) as well as mercury-organic compositions.

Agents for simultaneous use against nematodes and pathogenic soil fungi are likewise known, for instance sodium N-methyldithiocarbamate (British Pat. No. 789,690).

The object of the present invention is to provide agents of superior activity or other superior properties which have simultaneously fungicidal and nematocidal effects.

ESSENCE OF THE INVENTION

The compounds of the invention have the formula

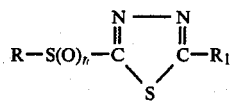

wherein R is $C_1$–$C_6$-alkyl, $C_2$–$C_6$-alkenyl, $C_2$–$C_6$-alkinyl or $C_3$–$C_6$-cycloalkyl, $R_1$ is $C_1$–$C_6$-alkoxycarbonyl, aminocarbonyl, $C_1$–$C_8$-alkylaminocarbonyl, $C_3$–$C_6$-cycloalkylaminocarbonyl, di-$C_1$–$C_8$-alkylaminocarbonyl, cyclohexylmethylaminocarbonyl, alkoxyalkylaminocarbonyl, morpholinocarbonyl, pyrrolidinocarbonyl, piperidinocarbonyl or cyano and n is 0, 1 or 2.

The compounds of the invention wherein n is 1 or 2 have a surprisingly broad spectrum of activity against phytopathogenic fungi, superior to prior art agents of the type above listed. They also have a good compatibility with agricultural plants and an adequate duration of their activity. They have furthermore the advantage that they are also effective against nematodes in which case they can be used, contrary to the prior art nematocidal compounds, without a waiting time between their use and the planting period because of their high plant compatibility. Thus, they permit a problem-free action against pests. A further advantage is that compared to the toxicologically objectionable mercury compounds they are environmentally acceptable.

Due to these properties the compounds of the invention can be used both in agricultural operations and in horticulture for treatment of the soil or for application to the leaves, etc.

The compounds of the invention wherein n is 1 or 2 have a superior activity against a large number of noxious fungi such as for instance *Pythium ultimum, Penicillium digitatum, Botrytis cinerea, Alternaria solani, Fusarium avenaceum, Tilletia caries, Helminthosporium gramineum, Ustilago avenae, Piricularia oryzae* and others.

The nematocidal activity is also effective against many genera of nematodes, for instance Meloidogyne sp., Rotylenchus, Pratylenchus, Tylenchorhynchus and others.

In the above formula I, R should preferably be methyl, ethyl, propyl, isopropyl, butyl, isobutyl, sec.-butyl, tert.-butyl, pentyl, isopentyl, neopentyl, hexyl, isohexyl, 2-propenyl, 2-propinyl, cyclopropyl and cyclohexyl.

$R_1$ preferably should be methoxycarbonyl, ethoxycarbonyl, aminocarbonyl, methylaminocarbonyl, butylaminocarbonyl, dimethylaminocarbonyl, cyclopropylaminocarbonyl, propylaminocarbonyl, isopropylaminocarbonyl, (N-butyl-N-methyl)-aminocarbonyl, (2-methoxyethyl)-aminocarbonyl, (3-methoxypropyl)-aminocarbonyl and cyano.

The compounds of the invention can either be used individually or intermixed with each other or intermixed with other active agents. If desired, other fungicidal, nematocidal or insecticidal compounds or other pesticides may be used depending on the specific purpose.

The compounds may be used in the form of compositions such as powders, dusting agents, granulates, solutions, emulsions or suspensions. There should then be added liquid and/or solid carrier materials or diluents and if desired surface active agents.

Suitable liquid carrier materials are water, mineral oils, or other organic solvents such as xylene, chlorobenzene, cyclohexanol, dioxane, acetonitrile, acetic ester, dimethylformamide, isophoron and dimethylsulfoxide.

As solid carrier materials there may be used lime, kaolin, chalk, talc, attaclay and other clays as well as natural or synthetic silicic acid.

If surface active agents are added they may for instance be salts of lignosulfonic acids, salts of alkylated benzoesulfonic acids, sulfonic acid amides and their salts, polyethoxyamines and alcohols.

If the agents are used for seed treatment there may be added dyestuffs in order to give the treated seed material a distinct coloration.

The fraction of the active agent or agents can be varied within a broad range. The particular concentration of the agents depends mainly on the amount of agent actually employed. For instance the total compositions may contain about 1 to 95% by weight, preferably 20 to 50% by weight, of active agent or agents and about 99 to 5% by weight of liquid or solid carrier materials. Part of the carrier materials may be replaced by up to 20% by weight of surface active agents.

The compositions may be applied in conventional form, for instance by spraying, dusting, fogging, gasifying, smoke formation, spreading, pouring or otherwise.

PROCESS OF MAKING THE PREFERRED COMPOUNDS (n = 1 or 2)

The compounds of the invention wherein n is 1 or 2 can be formed in various ways.

(A) Compounds of the formula

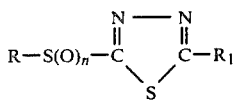

in which R and $R_1$ have the same meaning as in the above formula I and n is 0, are treated with oxidizing agents, preferably organic hydroperoxides, per-acids or inorganic oxidizing agents, in equimolar amounts dissolved in an inert solvent.

(B) Compounds of the invention wherein $R_1$ is a carboxylic acid amide residue can be made by reacting the compounds of the above formula II wherein, however, $R_1$ is $C_1$-$C_6$-alkoxycarbonyl with a suitable amine followed by treatment with an oxidizing agent as under A.

(C) If the compounds of formula I are intended to be of the type wherein $R_1$ is cyano they can be made by treating compounds of the above formula II wherein $R_1$ is aminocarbonyl with a dehydration agent followed by treatment with an oxidizing agent as described above at A.

(D) If the compounds of the invention are intended to be of the type wherein $R_1$ is a carboxylamide residue they can be made by reacting compounds of the formula

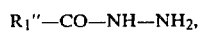

wherein $R_1''$ constitutes a carboxylic amide residue as listed with carbondisulfide in the presence of a base so as to form a compound of the formula

The latter product is then reacted with an alkylating agent to form a compound of the formula

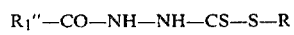

whereupon it is treated with a dehydration agent and an oxidizing agent in order to obtain the desired compounds of the invention.

(E) If compounds are wanted of the type of formula I in which $R_1$ is a carboxylic acid residue, the proceeding could be as follows: a compound of the formula

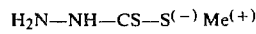

is reacted with an alkylating agent to form a compound of the formula

The latter reaction product is then treated with a compound of the formula

in which $R_1$ is $C_1$-$C_6$-alkoxycarbonyl so as to form a carboxylic acid derivative of the above formula II, the reaction being carried out under dehydrating conditions. The last obtained reaction product is then treated with an oxidizing agent as stated above at A.

In all these compounds R and $R_1$ have the meaning as in Formula I except as stated and $Me^{(+)}$ is a cation of an organic or inorganic base.

II. PROCESS FOR MAKING THE COMPOUNDS USED AS STARTING PRODUCTS BUT ALSO AS FINAL PRODUCTS (n=0)

The compounds of the formula I wherein n is 0 and which have not been disclosed heretofore can be made as follows:

Compounds of the formula

in which $R_1'$ is $C_1$-$C_6$-alkoxycarbonyl are reacted with carbon disulfide in the presence of a base so as to form a compound of the formula

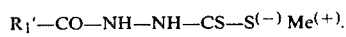

The latter reaction product is then reacted with a dehydration agent so as to form a compound of the formula

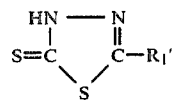

The latter compounds are subjected to the action of an alkylating agent, if desired in the presence of a base. There are thus formed the desired compounds of the formula

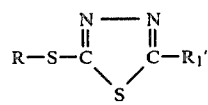

The latter may be further reacted with suitable amines to form compounds of the formula

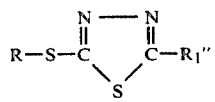

In all of these formulas R and $R_1$ have the meaning as in formula I unless otherwise indicated, $Me^{(+)}$ is the cation of an inorganic or organic base and $R_1''$ is a carboxylic amide residue or a cyano group.

III. DETAILS OF THE PROCESS OF MAKING

In order to make the compounds of the invention in which in the general formula I n=1 there may be used as oxidizing agents organic hydroperoxides such as tert.-butylhydroperoxide, or per-acids, such as m-chloroperbenzoic acid, or N-halogeno acid amides like N-bromosuccinimide. Inorganic oxidizing agents, such as hydrogen peroxide and sodium metaperiodate may also be used. Preferably two oxidation equivalents of the oxidizing agents or a small excess are employed per mol of thio compound at temperatures of about 0° to 60° C.

In order to make the compounds of the formula I in which n is 2 it is possible in addition to the just named oxidizing agents to use also agents such as chlorine, potassium permanganate, chromic acid and their salts or nitric acid and the temperature range of 0° to 120° C.

Preferably, there are used four oxidation equivalents or a slight excess above it per mol of thio compound. In other words, there are used about twice the amount of oxidizing agents as employed for the above-described sulfoxidation as in the case where n is 1.

The reaction in general can be carried out at temperatures between −30° and 120° C. These temperatures should be used during the oxidation reactions.

For the synthesis of the compounds of the invention the reactants are used in about equimolar amounts. This is otherwise in case of the dehydration reaction in which a large excess of the water extracting agent is preferred.

As reaction media there may be used solvents which are inert towards the reactants. They may be used as such or in mixture with water. Their selection dependson conventional considerations having in mind the specific purpose of the reaction. As solvents or suspension agents there may be used: carboxylic acids such as acetic acid, carboxylic amides, such as dimethylformamide; carboxylic acid nitriles, such as acetonitrile; alcohols, such as methanol; ethers, such as dioxane, and many others.

If it is considered advisable there may be used as inorganic or organic bases, oxides and hydroxides of the alkali or alkali earth metals, for instance sodium or potassium hydroxide or tertiary amines, such as triethylamine or N,N-dimethylaniline.

Suitable alkylating agents are for instance alkyl halides, preferably iodides and bromides, as well as esters of sulfuric acid, such as dimethylsulfate or esters of aromatic sulfonic acids, such as methyltosylate.

Suitable dehydration agents are particularly inorganic agents, such as mineral acids, for instance concentrated sulfuric acid or polyphosphoric acid, inorganic halides, for instance, phosphorus pentachloride, phosphorus trichloride, titanium tetrachloride and many others. Also organic agents may be used such as carboxylic acid chlorides, for instance acetylchloride, carboxylic acid anhydride, such as trifluoroacetic acid anhydride, carbodiimides, such as dicyclohexylcarbodiimide and many others. The isolation of the formed compounds of the invention may be carried out by distilling off the solvent at atmospheric or reduced pressure or by precipitation with water or a slightly polar organic solvent such as diethylether or by crystallization.

PREFERRED EMBODIMENTS OF THE INVENTION

Examples for compounds wherein n is 1 or 2.

The following examples will illustrate the making of compounds of the invention as shown in Formula I wherein n is 1 or 2.

EXAMPLE 1

5-ethylsulfonyl-1,3,4-thiadiazole-2-carboxylic acid ethylamide

A solution of 20.0 g of 5-ethylthio-1,3,4-thiadiazole-2-carboxylic acid ethylamide in 70 ml of acetic acid is heated to 80° C. When this temperature is reached 31.3 g of a 30% concentration of aqueous hydrogen peroxide are added dropwise resulting in boiling of the solution. When no more heat development is observed the solution is subjected to another hour of reflux boiling whereupon it is cooled to room temperature, stirred in ice water and subjected to removal by suction of the precipitated compound.

Yield: 17.8 g (78% of the theoretical value); M.p.: 116° C.

EXAMPLE 2

5-ethylsulfinyl-1,3,4-thiadiazole-2-carboxamide 38 g of 5-ethylthio-1,3,4-thiadiazole-2-carboxamide are dissolved at 40° C. in 400 ml of glacial acetic acid and are then slowly reacted with 22.6 ml of a 30% hydrogen peroxide upon stirring. The solution is kept for another 3 hours at the same temperature. At the end of this period the oxidation is sufficiently complete not to require any further addition of heat. After standing overnight the reaction mixture is stirred into two liters of icewater resulting in the precipitation of a solid material which is removed by suction and recrystallized from isopropanol.

Yield: 15.2 g (37% of the theoretical value); M.p.: 103° C.

EXAMPLE 3

5-methylsulfonyl-1,3,4-thiadiazole-2-carboxamide 9.3 g of 5-methylthio-1,3,4-thiadiazole-2-carboxamide were dissolved at 80° C. in 50 ml acetic acid and were reacted with 18 ml of 30% hydrogen peroxide upon stirring so as to permit to keep the solution during boiling under reflux. After the addition is complete the boiling was continued for 30 minutes. After cooling to room temperature the reaction product precipitated. It was removed by suction and dried.

Yield: 7.3 g (67% of the theoretical value); M.p.: 185° C.

EXAMPLE 4

5-isopropylsulfonyl-1,3,4-thiadiazole-2-carbonitrile 40 ml of 30% hydrogen peroxide were added dropwise under stirring at 70° C. to a solution of 46.0 g of 5-isopropylthio-1,3,4-thiadiazole-2-carboxamide in 250 ml of glacial acetic acid. This caused the solution to boil. Then 40 ml of perhydrol were furthermore added causing the reaction solution to remain boiling without addition of any heat. The mixture was then subjected to stirring for another 30 minutes whereupon it was cooled which caused the reaction product to crystallize out at 30° C. By adding icewater the precipitation was completed. The crystallate was removed by suction and dried in a vacuum.

Yield: 45.0 g (86% of the theoretical amount); M.p.: 162° C.

EXAMPLE 5

5-methylsulfonyl-1,3,4-thiadiazole-2-carbonitrile

A mixture of 20 ml titanium tetrachloride in 50 ml carbon tetrachloride was added dropwise at 0° to 5° C. upon stirring to 350 ml tetrahydrofuran. Subsequently, 2-methylsulfonyl-1,3,4-thiadiazole-2-carboxamide was added in batches at room temperature in an amount of 20.7 g. After continued stirring for 1 hour a solution of 50 ml triethylamine in 50 ml tetrahydrofuran was dropped into the mixture within a period of 60 minutes. The mixture was then reacted with 50 ml water, the total mixture was extracted with chloroform and the organic phase was dried over magnesium sulfate and the solvent was distilled off in a vacuum. The residue was taken up in acetic acid ethylester, subjected to boiling with activated carbon, filtered and concentrated. The residue was crystallized from chloroform/tetrahydrofuran (3:1).

Yield: 9.1 g (48% of the theoretical value); M.p.: 173°–175° C.

EXAMPLE 6

5-methylsulfonyl-1,3,4-thiadiazole-2-carboxylic acid ethylester 21.4 g of powdered potassium permanganate was introduced into a solution of 20.4 g of 5-methylthio-1,3,4-thiadiazole-2-carboxylic acid ethylester in 100 ml acetic acid and 40 ml water in a manner that the temperature of the solution rose to 70° C. To complete the reaction the mixture was stirred for another 30 minutes. Thereafter, the manganese dioxide which precipitated at 10° was reduced with a solution of 19 g sodium metabisulfite in 100 ml water while cooling with ice. Upon addition of 500 ml water the desired compound precipitated. It was removed by suction, dried and recrystallized from isopropylether.

Yield: 9.4 g (40% of the theoretical value); M.p.: 48° C.

EXAMPLE 7

5-methylsulfonyl-1,3,4-thiadiazole-2-carboxylic acid cyclohexylmethylamide 20.3 g of 5-methylthio-1,3,4-thiadiazole-2-carboxylic acid cyclohexylmethylamide were dissolved in 130 ml acetic acid and 25 ml water. 16 g pulverized potassium permanganate was then introduced upon stirring to cause the temperature to increase to 70° C. Thereafter, stirring was continued for 30 minutes. The mixture was cooled and then mixed with 300 ml ice water. The formed manganese dioxide was reduced with a solution of 14.3 g sodium metabisulfite in 100 ml water. The precipitated compound was removed by suction and recrystallized from ethanol.

Yield: 18.3 g (81% of the theoretical value); M.p.: 159° C.

In an analogous manner to the Examples 1 to 7 the following specific compounds were made:

| Compound | Physical constants |
|---|---|
| 5-ethylsulfonyl-1,3,4-thiadiazole-2-carboxamide | M.p.: 143° C. |
| 5-ethylsulfonyl-1,3,4-thiadiazole-2-carbonitrile | M.p.: 87° C. |
| 5-isopropylsulfonyl-1,3,4-thiadiazole-2-carbonitrile | M.p.: 78° C. |
| 5-methylsulfonyl-1,3,4-thiadiazole-2-carboxylic acid methylamide | M.p.: 135° C. |
| 5-methylsulfonyl-1,3,4-thiadiazole-2-carboxylic acid-dimethylamide | M.p.: 91° C. |
| 5-isobutylsulfonyl-1,3,4-thiadiazole-2-carboxamide | M.p.: 125° C. |
| 5-ethylsulfonyl-1,3,4-thiadiazole-2-carboxylic acid-methylamide | M.p.: 169° C. |
| 5-ethylsulfinyl-1,3,4-thiadiazole-2-carboxylic acid-dimethylamide | M.p.: 58° C. |
| 5-propylsulfonyl-1,3,4-thiadiazole-2-carboxamide | M.p.: 153° C. |
| 5-propylsulfonyl-1,3,4-thiadiazole-2-carboxylic acid-methylamide | M.p.: 148° C. |
| 5-ethylsulfonyl-1,3,4-thiadiazole-2-carboxylic acid-butylamide | M.p.: 77° C. |
| 5-ethylsulfonyl-1,3,4-thiadiazole-2-carboxylic acid-ethylester | M.p.: 55° C. |
| 5-ethylsulfonyl-1,3,4-thiadiazole-2-carboxylic acid-cyclopropylamide | M.p.: 135° C. |
| 5-methylsulfonyl-1,3,4-thiadiazole-2-carboxylic acid-methylester | M.p.: 95° C. |
| 5-ethylsulfonyl-1,3,4-thiadiazole-2-carboxylic acid-propylamide | M.p.: 105° C. |
| 5-ethylsulfonyl-1,3,4-thiadiazole-2-carboxylic acid-(N-butyl,N-methyl)-amide | $n_D^{20}$: 1,5310 |
| 5-ethylsulfonyl-1,3,4-thiadiazole-2-carboxylic acid-(2-methoxyethyl)-amide | M.p.: 77° C. |
| 5-ethylsulfonyl-1,3,4-thiadiazole-2-carboxylic acid-(3-methoxypropyl)-amide | M.p.: 71° C. |
| 5-ethylsulfonyl-1,3,4-thiadiazole-2-carboxylic acid-isopropylamide | M.p.: 85° C. |
| 5-ethylsulfonyl-1,3,4-thiadiazole-2-carboxylic acid-allylamide | M.p.: 61° C. |
| 5-ethylsulfonyl-1,3,4-thiadiazole-2-carboxylic acid-octylamide | M.p.: 82° C. |
| 5-ethylsulfonyl-1,3,4-thiadiazole-2-carboxylic acid-N,N-tetramethylene-amide | M.p.: 91° C. |
| 5-ethylsulfonyl-1,3,4-thiadiazole-2-carboxylic acid-(N,N-3-oxapentamethylene amide | M.p.: 83° C. |
| 5-ethylsulfonyl-1,3,4-thiadiazole-2-carboxylic acid-cyclooctylamide | M.p.: 97° C. |
| 5-propylsulfonyl-1,3,4-thiadiazole-2-carboxylic acid-ethylester | M.p.: 38° C. |
| 5-propylsulfonyl-1,3,4-thiadiazole-2-carbonitrile | M.p.: 83° C. |
| 5-propylsulfinyl-1,3,4-thiadiazole-2-carbonitrile | M.p.: 69° C. |
| 5-ethylsulfinyl-1,3,4-thiadiazole-2-carbonitrile | M.p.: 78° C. |
| 5-methylsulfonyl-1,3,4-thiadiazole-2-carboxylic acid-ethylamide | M.p.: 137° C. |
| 5-methylsulfonyl-1,3,4-thiadiazole-2-carboxylic acid-isopropylamide | M.p.: 108° C. |
| 5-methylsulfonyl-1,3,4-thiadiazole-2-carboxylic acid-propylamide | M.p.: 115° C. |
| 5-methylsulfonyl-1,3,4-thiadiazole-2-carboxylic acid-butylamide | M.p.: 95° C. |
| 5-methylsulfinyl-1,3,4-thiadiazole-2-carboxylic acid-propylamide | M.p.: 95° C. |
| 5-methylsulfinyl-1,3,4-thiadiazole-2-carboxylic acid-butylamide | M.p.: 88° C. |
| 5-propylsulfonyl-1,3,4-thiadiazole-2-carboxylic acid-ethylamide | M.p.: 105° C. |
| 5-propylsulfonyl-1,3,4-thiadiazole-2-carboxylic acid-propylamide | M.p.: 103° C. |
| 5-propylsulfonyl-1,3,4-thiadiazole-2-carboxylic acid-allylamide | M.p.: 70° C. |
| 5-sec.-butylsulfonyl-1,3,4-thiadiazole-2-carboxylic acid-ethylester | $n_D^{20}$: 1,5168 |
| 5-sec.-butylsulfonyl-1,3,4-thiadiazole-2-carboxamide | M.p.: 127° C. |
| 5-methylsulfinyl-1,3,4-thiadiazole-2-carboxylic acid-allylamide | M.p.: 68° C. |
| 5-sec.-butylsulfinyl-1,3,4-thiadiazole-2-carboxamide | M.p.: 87° C. |
| 5-sec.-butylsulfonyl-1,3,4-thiadiazole-2-carbonitrile | M.p.: 57° C. |
| 5-propylsulfonyl-1,3,4-thiadiazole-2-carboxylic acid-isopropylamide | M.p.: 79° C. |
| 5-propylsulfonyl-1,3,4-thiadiazole-2-carboxylic acid-butylamide | M.p.: 88° C. |
| 5-methylsulfonyl-1,3,4-thiadiazole-2-2-carboxylic acid-allylamide | M.p.: 72° C. |
| 5-propylsulfinyl-1,3,4-thiadiazole-2-carboxylic acid-ethylamide | M.p.: 75° C. |
| 5-propylsulfinyl-1,3,4-thiadiazole-2-carboxylic acid-propylamide | M.p.: 67° C. |
| 5-propylsulfinyl-1,3,4-thiadiazole-2-carboxylic acid-allylamide | M.p.: 73° C. |
| 5-propylsulfinyl-1,3,4-thiadiazole-2-carboxylic acid-isopropylamide | M.p.: 76° C. |
| 5-methylsulfinyl-1,3,4-thiadiazole-2-carboxylic acid-(2-methoxyethyl)-amide | M.p.: 63° C. |
| 5-methylsulfonyl-1,3,4-thiadiazole-2-carboxylic acid-(2-methoxyethyl)-amide | M.p.: 80° C. |
| 5-methylsulfonyl-1,3,4-thiadiazole-2-carboxylic acid-(3-methoxypropyl)-amide | M.p.: 97° C. |

| Compound | Physical constants |
|---|---|
| 5-methylsulfinyl-1,3,4-thiadiazole-2-carboxylic acid-(3-methoxypropyl)-amide | M.p.: 71° C. |
| 5-methylsulfinyl-1,3,4-thiadiazole-2-carboxylic acid-ethylamide | M.p.: 118° C. |
| 5-methylsulfinyl-1,3,4-thiadiazole-2-carboxylic acid-isopropylamide | M.p.: 77° C. |
| 5-methylsulfonyl-1,3,4-thiadiazole-2-carboxylic acid-cyclopropylamide | M.p.: 171° C. |
| 5-methylsulfinyl-1,3,4-thiadiazole-2-carboxylic acid-cyclopropylamide | M.p.: 149° C. |
| 5-methylsulfonyl-1,3,4-thiadiazole-2-carboxylic acid-N,N-trimethylenamide | M.p.: 144° C. |
| 5-methylsulfinyl-1,3,4-thiadiazole-2-carboxylic acid-N,N-trimethylenamide | M.p.: 135° C. |
| 5-propylsulfonyl-1,3,4-thiadiazole-2-carboxylic acid-sec.-butylamide | M.p.: 45° C. |
| 5-propylsulfonyl-1,3,4-thiadiazole-2-carboxylic acid-dimethylamide | M.p.: 75° C. |
| 5-butylsulfonyl-1,3,4-thiadiazole-2-carboxamide | M.p.: 135° C. |
| 5-butylsulfinyl-1,3,4-thiadiazole-2-carboxamide | M.p.: 105° C. |
| 5-butylsulfonyl-1,3,4-thiadiazole-2-carbonitrile | M.p.: 43° C. |
| 5-isobutylsulfonyl-1,3,4-thiadiazole-2-carbonitrile | M.p.: 72° C. |
| 5-propylsulfonyl-1,3,4-thiadiazole-2-carboxylic acid-hexylamide | M.p.: 75° C. |
| 5-isopropylsulfonyl-1,3,4-thiadiazole-2-carboxylic acid-cyclohexylmethylamide | M.p.: 134° C. |
| 5-isopropylsulfinyl-1,3,4-thiadiazole-2-carboxylic acid-cyclohexylmethylamide | M.p.: 139° C. |
| 5-propylsulfinyl-1,3,4-thiadiazole-2-carboxylic acid-butylamide | M.p.: 64° C. |
| 5-propylsulfinyl-1,3,4-thiadiazole-2-carboxylic acid-sec.-butylamide | M.p.: 60° C. |
| 5-propylsulfinyl-1,3,4-thiadiazole-2-carboxylic acid-hexylamide | M.p.: 68° C. |
| 5-propylsulfinyl-1,3,4-thiadiazole-2-carboxylic acid-dimethylamide | M.p.: 64° C. |
| 5-methylsulfinyl-1,3,4-thiadiazole-2-carbonitrile | M.p.: 114° C. |
| 5-methylsulfinyl-1,3,4-thiadiazole-2-carboxamide | M.p.: 163° C. |
| 5-isopropylsulfinyl-1,3,4-thiadiazole-2-carboxamide | M.p.: 135° C. (decomposed) |
| 5-isopropylsulfinyl-1,3,4-thiadiazole-2-carbonitrile | $n_D^{20}$: 1,5812 |
| 5-pentylsulfonyl-1,3,4-thiadiazole-2-carboxylic acid-ethylester | $n_D^{20}$: 1,5130 |
| 5-pentylsulfonyl-1,3,4-thiadiazole-2-carbonitrile | M.p.: 51° C. |
| 5-hexylsulfonyl-1,3,4-thiadiazole-2-carbonitrile | M.p.: 39° C. |
| 5-pentylsulfonyl-1,3,4-thiadiazole-2-carboxamide | M.p.: 151° C. |
| 5-hexylsulfonyl-1,3,4-thiadiazole-2-carboxamide | M.p.: 139° C. |
| 5-propylsulfonyl-1,3,4-thiadiazole-2-carboxylic acid-N,N-trimethyleneamide | M.p.: 127° C. |
| 5-butylsulfonyl-1,3,4-thiadiazole-2-carboxylic acid-N,N-trimethylenamide | M.p.: 102° C. |
| 5-butylsulfinyl-1,3,4-thiadiazole-2-carbonitrile | M.p.: 68° C. |
| 5-ethylsulfonyl-1,3,4-thiadiazole-2-carboxylic acid-N,N-trimethyleneamide | M.p.: 107° C. |
| 5-isopropylsulfonyl-1,3,4-thiadiazole-2-carboxylic acid-methylamide | M.p.: 207° C. |
| 5-isopropylsulfonyl-1,3,4-thiadiazole-2-carboxylic acid-ethylamide | M.p.: 131° C. |
| 5-isopropylsulfonyl-1,3,4-thiadiazole-2-carboxylic acid-isopropylamide | M.p.: 111° C. |
| 5-isopropylsulfonyl-1,3,4-thiadiazole-2-carboxylic acid-propylamide | M.p.: 94° C. |
| 5-isopropylsulfonyl-1,3,4-thiadiazole-2-carboxylic acid-butylamide | M.p.: 72° C. |
| 5-isopropylsulfonyl-1,3,4-thiadiazole-2-carboxylic acid-isobutylamide | M.p.: 92° C. |
| 5-isopropylsulfonyl-1,3,4-thiadiazole-2-carboxylic acid-sec.-butylamide | M.p.: 92° C. |
| 5-isopropylsulfinyl-1,3,4-thiadiazole-2-carboxylic acid-methylamide | M.p.: 184 (decomposed) |
| 5-isopropylsulfinyl-1,3,4-thiadiazole-2-carboxylic acid-ethylamide | M.p.: 118° C. |
| 5-(2-propenylsulfinyl)-1,3,4-thiadiazole-2-carboxylic acid-methylamide | M.p.: 125° C. |
| 5-methylsulfonyl-1,3,4-thiadiazole-2-carboxylic acid-N-ethyl-N-butylamide | $n_D^{20}$: 1,5312 |
| 5-isopropylsulfinyl-1,3,4-thiadiazole-2-carboxylic acid-propylamide | M.p.: 84° C. |
| 5-isopropylsulfonyl-1,3,4-thiadiazole-2-carboxylic acid-isopropylamide | M.p.: 84° C. |
| 5-isopropylsulfonyl-1,3,4-thiadiazole-2-carboxylic acid-dimethylamide | M.p.: 82° C. |
| 5-butylsulfonyl-1,3,4-thiadiazole-2-carboxylic acid-methylamide | M.p.: 146° C. |
| 5-butylsulfonyl-1,3,4-thiadiazole-2-carboxylic acid-ethylamide | M.p.: 87° C. |
| 5-butylsulfonyl-1,3,4-thiadiazole-2-carboxylic acid-propylamide | M.p.: 101° C. |
| 5-butylsulfonyl-1,3,4-thiadiazole-2-carboxylic acid-(2-methoxyethyl)amide | M.p.: 63° C. |
| 5-butylsulfonyl-1,3,4-thiadiazole-2-carboxylic acid-isopropylamide | M.p.: 99° C. |
| 5-butylsulfinyl-1,3,4-thiadiazole-2-carboxylic acid-methylamide | M.p.: 112° C. |
| 5-butylsulfinyl-1,3,4-thiadiazole-2-carboxylic acid-ethylamide | M.p.: 72° C. |
| 5-butylsulfinyl-1,3,4-thiadiazole-2-carboxylic acid-propylamide | M.p.: 84° C. |
| 5-butylsulfinyl-1,3,4-thiadiazole-2-carboxylic acid-(2-methoxyethyl)-amide | M.p.: 54° C. |
| 5-butylsulfinyl-1,3,4-thiadiazole-2-carboxylic acid-isopropylamide | M.p.: 57° C. |
| 5-methylsulfonyl-1,3,4-thiadiazole-2-carboxylic acid-N-butyl-N-methylamide | $n_D^{20}$: 1,5330 |
| 5-methylsulfonyl-1,3,4-thiadiazole-2-carboxylic acid-N-isobutyl-N-methyl- | $n_D^{20}$: 1,5291 |
| 5-methylsulfonyl-1,3,4-thiadiazole-2-carboxylic acid-N,N-diethylamide | M.p.: 98° C. |
| 5-sec.-butylsulfonyl-1,3,4-thiadiazole-2-carboxylic acid-methylamide | M.p.: 150° C. |
| 5-sec.-butylsulfonyl-1,3,4-thiadiazole-2-carboxylic acid-ethylamide | M.p.: 79° C. |
| 5-cyclohexylsulfonyl-1,3,4-thiadiazole-2-carboxamide | M.p.: 176° C. |
| 5-cyclohexylsulfonyl-1,3,4-thiadiazole-2-carbonitrile | M.p.: 140° C. |
| 5-methylsulfonyl-1,3,4-thiadiazole-2-carboxylic acid-N,N-dipropylamide | M.p.: 55° C. |
| 5-sec.-butylsulfonyl-1,3,4-thiadiazole-2-carboxylic acid-cyclopropylamide | M.p.: 95° C. |
| 5-pentylsulfinyl-1,3,4-thiadiazole-2-carbonitrile | M.p.: 65° C. |
| 5-hexylsulfinyl-1,3,4-thiadiazole-2-carbonitrile | M.p.: 57° C. |
| 5-pentylsulfonyl-1,3,4-thiadiazole-2-carboxylic acid-methylamide | M.p.: 126° C. |
| 5-hexylsulfonyl-1,3,4-thiadiazole-2-carboxylic acid-methylamide | M.p.: 108° C. |
| 5-cyclohexylsulfinyl-1,3,4-thiadiazole-2-carbonitrile | M.p.: 87° C. |
| 5-sec.-butylsulfonyl-1,3,4-thiadiazole-2-carboxylic acid-(2-methoxyethyl)amide | $n_D^{20}$: 1,5357 |
| 5-sec.-butylsulfinyl-1,3,4-thiadiazole-2-carboxylic acid-methylamide | M.p.: 115° C. |
| 5-sec.-butylsulfinyl-1,3,4-thiadiazole-2-carboxylic acid-ethylamide | $n_D^{20}$: 1,5580 |
| 5-pentylsulfonyl-1,3,4-thiadiazole-2-carboxylic acid-ethylamide | M.p.: 90° C. |
| 5-hexylsulfonyl-1,3,4-thiadiazole-2-carboxylic acid-ethylamide | M.p.: 67° C. |
| 5-pentylsulfinyl-1,3,4-thiadiazole-2-carboxylic acid-ethylamide | M.p.: 75° C. |
| 5-hexylsulfinyl-1,3,4-thiadiazole-2-carboxylic acid-ethylamide | M.p.: 75° C. |
| 5-methylsulfinyl-1,3,4-thiadiazole-2-carboxylic acid-N,N-diethylamide | $n_D^{20}$: 1,5650 |

| Compound | Physical constants |
|---|---|
| 5-sec.-butylsulfonyl-1,3,4-thiadiazole-2-carboxylic acid-isopropylamide | M.p.: 77° C. |
| 5-sec.-butylsulfinyl-1,3,4-thiadiazole-2-carboxylic acid-cyclopropylamide | $n_D^{20}$: 1,5671 |
| 5-pentylsulfonyl-1,3,4-thiadiazole-2-carboxylic acid-propylamide | M.p.: 86° C. |
| 5-pentylsulfonyl-1,3,4-thiadiazole-2-carboxylic acid-isopropylamide | M.p.: 95° C. |
| 5-pentylsulfonyl-1,3,4-thiadiazole-2-carboxylic acid-cyclopropylamide | M.p.: 106° C. |
| 5-pentylsulfonyl-1,3,4-thiadiazole-2-carboxylic acid-butylamide | M.p.: 92° C. |
| 5-pentylsulfonyl-1,3,4-thiadiazole-2-carboxylic acid-sec.-butylamide | M.p.: 89° C. |
| 5-pentylsulfonyl-1,3,4-thiadiazole-2-carboxylic acid-isobutylamide | M.p.: 106° C. |
| 5-pentylsulfinyl-1,3,4-thiadiazole-2-carboxylic acid-propylamide | M.p.: 79° C. |
| 5-pentylsulfinyl-1,3,4-thiadiazole-2-carboxylic acid-isopropylamide | M.p.: 61° C. |
| 5-pentylsulfinyl-1,3,4-thiadiazole-2-carboxylic acid-allylamide | M.p.: 74° C. |
| 5-pentylsulfinyl-1,3,4-thiadiazole-2-carboxylic acid-cyclopropylamide | M.p.: 90° C. |
| 5-pentylsulfinyl-1,3,4-thiadiazole-2-carboxylic acid-butylamide | M.p.: 85° C. |
| 5-pentylsulfinyl-1,3,4-thiadiazole-2-carboxylic acid-sec.-butylamide | M.p.: 59° C. |
| 5-pentylsulfinyl-1,3,4-thiadiazole-2-carboxylic acid-isobutylamide | M.p.: 80° C. |
| 5-cyclopentylsulfonyl-1,3,4-thiadiazole-2-carboxylic acid-methylamide | M.p.: 203° C. |
| 5-cyclopentylsulfonyl-1,3,4-thiadiazole-2-carboxylic acid-ethylamide | M.p.: 115° C. |
| 5-sec.-butylsulfinyl-1,3,4-thiadiazole-2-carboxylic acid-(2-methoxyethyl)-amide | $n_D^{20}$: 1,5519 |
| 5-sec.-butylsulfonyl-1,3,4-thiadiazole-2-carboxylic acid-(3-methoxypropyl)-amide | $n_D^{20}$: 1,5324 |
| 5-cyclopentylsulfonyl-1,3,4-thiadiazole-2-carboxylic acid-propylamide | M.p.: 95° C. |
| 5-cyclopentylsulfonyl-1,3,4-thiadiazole-2-carboxylic acid-isopropylamide | M.p.: 77° C. |
| 5-cyclopentylsulfonyl-1,3,4-thiadiazole-2-carboxylic acid-cyclopropylamide | M.p.: 90° C. |
| 5-cyclopentylsulfonyl-1,3,4-thiadiazole-2-carboxylic acid-butylamide | M.p.: 76° C. |
| 5-cyclopentylsulfonyl-1,3,4-thiadiazole-2-carboxylic acid-dimethylamide | M.p.: 56° C. |
| 5-pentylsulfonyl-1,3,4-thiadiazole-2-carboxylic acid-dimethylamide | M.p.: 61° C. |
| 5-pentylsulfonyl-1,3,4-thiadiazole-2-carboxylic acid-(3-methoxypropyl)-amide | M.p.: 56° C. |
| 5-hexylsulfonyl-1,3,4-thiadiazole-2-carboxylic acid-propylamide | M.p.: 80° C. |
| 5-hexylsulfonyl-1,3,4-thiadiazole-2-carboxylic acid-isopropylamide | M.p.: 91° C. |
| 5-hexylsulfonyl-1,3,4-thiadiazole-2-carboxylic acid-(2-methoxyethyl)-amide | M.p.: 46° C. |
| 5-hexylsulfonyl-1,3,4-thiadiazole-2-carboxylic acid-(3-methoxypropyl)-amide | M.p.: 57° C. |
| 5-cyclopentylsulfinyl-1,3,4-thiadiazole-2-carboxylic acid-methylamide | M.p.: 168° C. (decomposed) |
| 5-cyclopentylsulfinyl-1,3,4-thiadiazole-2-carboxylic acid-ethylamide | M.p.: 93° C. |
| 5-methylsulfonyl-1,3,4-thiadiazole-2-carboxylic acid-N,N-diisopropylamide | $n_D^{20}$: 1,5240 |
| 5-sec.-butylsulfinyl-1,3,4-thiadiazole-2-carboxylic acid-(3-methoxypropyl)-amide | $n_D^{20}$: 1,5489 |
| 5-hexylsulfinyl-1,3,4-thiadiazole-2-carboxylic acid-propylamide | M.p.: 71° C. |
| 5-hexylsulfinyl-1,3,4-thiadiazole-2-carboxylic acid-isopropylamide | M.p.: 61° C. |
| 5-hexylsulfinyl-1,3,4-thiadiazole-2-carboxylic acid-(2-propenyl)-amide | M.p.: 69° C. |
| 5-hexylsulfinyl-1,3,4-thiadiazole-2-carboxylic acid-cyclopropylamide | M.p.: 90° C. |
| 5-hexylsulfinyl-1,3,4-thiadiazole-2-carboxylic acid-(2-methoxyethyl)-amide | M.p.: 57° C. |
| 5-hexylsulfonyl-1,3,4-thiadiazole-2-carboxylic acid-cyclopropylamide | M.p.: 83° C. |
| 5-hexylsulfinyl-1,3,4-thiadiazole-2-carboxylic acid-(3-methoxypropyl)-amide | M.p.: 53° C. |

The compounds of the invention are colorless and non-smelling oils or crystalline bodies which have a good solubility in polar organic solvents such as carboxylic acid amides, for instance dimethylformamide; carboxylic acid nitriles, for instance acetonitrile, and alcohols such as methanol. They are less soluble in hydrocarbons, for instance hexane, and halogenated hydrocarbons, for instance dichloromethane. They are insoluble in water.

EXAMPLES ILLUSTRATING THE STARTING PRODUCTS AND COMPOUNDS OF THE INVENTION WHEREIN N=0.

The following examples illustrate the making of the compounds of the invention coming under formula I wherein n=0. These compounds are starting products or intermediate products for making the compounds of the invention in which n is 1 or 2. However, in view of their partial nematocidal properties they may also be used directly as nematocides in agriculture and horticulture.

EXAMPLE 8

(a) 3-(ethoxyoxalyl)-dithiocarbazinic acid, potassium salt 91.5 g of carbon disulfide were added upon stirring to a suspension of 198 g of oxalic acid ethylesterhydrazide in 1 l ethanol while stirring. At a temperature between 10° and 15° C. there was then added dropwise a solution of 98.7 g of 85% concentration potassium hydroxide in 900 ml ethanol. Stirring was continued for 1 hour and the formed salt was extracted with 3 l diethylether. The potassium salt was removed by suction, washed with ether and dried in a vacuum.

Yield: 357 g (97% of the theoretical amount);
M.p. : 160° C.

(b) 5-thioxo-1,3,4-thiadiazoline-2-carboxylic acid ethylester 440 g of the product obtained in (a), that is 3-(ethoxyoxalyl)-dithiocarbazinic acid, potassium salt were introduced into 1.2 l concentrated sulfuric acid at a temperature of 20°-30° C. The mixture was stirred until the compounds was completely dissolved. After standing overnight the solution was stirred in 5 l icewater. The percipitated compound was removed by suction, washed with water, and dried in a vacuum at 40° C.

Yield: 163.5 g (48% of the theoretical value);
M.p. : 91° C.

(c) 5-ethylthio-1,3,4-thiadiazole-2-carboxylic acid ethylester 99.9 g of ethyliodide were added to a suspension of 121.3 g of the compound obtained in (b), i.e. 5-thioxo-1,3,4-thiadiazoline-2-carboxylic acid ethylester in 350 ml ethanol. Thereafter, 64.7 g of triethylamine were added dropwise at a temperature between 20° and 25° C. while cooling and stirring the mixture. Stirring was then continued for another 2 hours. The mixture was thereafter poured into 1.5 l icewater. The precipitating oil was extracted with 300 ml chloroform. The chloroform phase was separated, twice washed with water and dried on magnesium sulfate. The solvent was distilled off at a reduced pressure.

Yield: 99.3 g (71% of the theoretical value);
$n_D^{20}$: 1,5782.

EXAMPLE 9

5-ethylthio-1,3,4-thiadiazole-2-carboxylic acid ethylamide 54 g of an aqueous 50% ethylamine solution were added to 43.7 g of the compound obtained in Example 8(c), that is ethylthio-1,3,4-thiadiazole-2-carboxylic acid ethyester. This caused the temperature to rise to 46° C. The solution was subsequently heated to boiling point for another 15 minutes. It was then cooled to 4° C. and reacted with 50 ml icewater. The precipitated compound was removed by suction.

Yield: 30.0 g (69% of the theoretical value);
M.p. : 85° C.

EXAMPLE 10

5-methylthio-1,3,4-thiadiazole-2-carboxylic acid ethylester 61 g of dithiocarbazinic acid methylester were dissolved in 400 ml dioxane. By adding dropwise upon stirring 75 g of oxalic acid ethylesterchloride, the temperature was caused to rise to 75° C. At this temperature the solution was subjected to further stirring for 30 minutes. The dioxane was distilled off in a vacuum and the oily residue was introduced in 350 ml of concentrated sulfuric acid. To complete the cyclization the reaction solution was kept for another hour at 40° C. and after cooling to room temperature was stirred into 2 l icewater. The precipitated crystals were removed by suction and recrystallized from cyclohexane.

Yield: 68.5 g (67% of the theoretical value);
M.p. : 46° C.

EXAMPLE 11

5-methylthio-1,3,4-thiadiazole-2-carboxamide 11.8 g of 5-methylthio-1,3,4-thiadiazole-2-carboxylic acid ethylester which is the compound obtained in Example 10, were mixed with 50 ml ethanol and 50 ml of a 25% aqueous ammonia solution whereupon the mixture was heated for 15 minutes on a steam bath. After cooling part of the reaction product precipitated. The precipitation was completed by adding ice water. The precipitate was then removed by suction and dried in a vacuum.

Yield: 8.9 g (88% of the theoretical amount);
M.p. : 185° C.

EXAMPLE 12

5-methylthio-1,3,4-thiadiazole-2-carbonitrile 350 ml tetrahydrofuran were added dropwise upon stirring and cooling at a temperature between 0° and 5° C. to a solution of 20 ml titanium tetrachloride in 50 ml carbon tetrachloride. There were then added at first in batches 15.3 g of 5-methylthio-1,3,4-thiadiazole-2-carboxamide as obtained in Example 11, and thereafter within a period of 1 hour 50 ml triethylamine which had been taken up in 50 ml tetrahydrofuran. After addition of 50 ml water the reaction mixture was extracted with chloroform. The extract was dried on magnesium sulfate and the solvent was removed in a vacuum. The residue was taken up in acetic acid ethylester and filtrated off from the insoluble residue. The ester phase was then treated with activated carbon and finally concentrated to dryness in a vacuum.

Yield: 11.1 g (81% of the theoretical amount);
M.p. : 118°–120° C.

EXAMPLE 13

5-methylthio-1,3,4-thiadiazole-2-carboxylic acid cyclohexyl methylamide 30.6 g of 5-methylthio-1,3,4-thiadiazole-2-carboxylic acid ethylester as obtained in Example 10, were heated to boiling point for 2 hours with 16.95 g of cyclohexylmethylamine in 150 ml ethanol. The solution was concentrated to 50 ml and the reaction product was precipitated by stirring in ice water.

Yield: 35.3 g (87% of the theoretical value);
M.P. : 103° C.

In a manner analogous to the processes of Examples 8 to 13 the following further starting products or intermediate products were obtained.

| Compound | Physical Constants |
|---|---|
| 5-methylthio-1,3,4-thiadiazole-2-carboxylic acid methylester | M.p.: 80° C. |
| 5-methylthio-1,3,4-thiadiazole-2-carboxylic acid methylamide | M.p.: 128° C. |
| 5-methylthio-1,3,4-thiadiazole-2-carboxylic acid dimethylamide | M.p.: 128° C. |
| 5-ethylthio-1,3,4-thiadiazole-2-carboxamide | M.p.: 162° C. |
| 5-ethylthio-1,3,4-thiadiazole-2-carboxylic acid methylamide | M.p.: 116° C. |
| 5-ethylthio-1,3,4-thiadiazole-2-carboxylic acid dimethylamide | M.p: 53° C. |
| 5-ethylthio-1,3,4-thiadiazole-2-carboxylic acid cyclopropylamide | M.p.: 91° C. |
| 5-ethylthio-1,3,4thiadiazole-2-carboxylic acid butylamide | M.p.: 54° C. |
| 5-propylthio-1,3,4-thiadiazole-2-carboxamide | M.p.: 137° C. |
| 5-propylthio-1,3,4-thiadiazle-2-carboxylic acid methylamide | M.p.: 72° C. |
| 5-isopropylthio-1,3,4-thiadiazole-2-carboxamide | M.p.: 154° C. |
| 5-isobutylthio-1,3,4-thiadiazole-2-carboxamide | M.p.: 162° C. |
| 5-ethylthio-1,3,4-thiadiazole-2-carbonitrile | M.p.: 40° C. |
| 5-propylthio-1,3,4-thiadiazole-2-carboxamide | M.p.: 142° C. |
| 5-sec.-butylthio-1,3,4-thiadiazole-2-carboxamide | M.p.: 119° C. |
| 5-methylthio-1,3,4-thiadiazole-2-carboxylic acid-propylamide | M.p.: 83° C. |
| 5-methylthio-1,3,4-thiadiazole-2-carboxylic acid-butylamide | M.p.: 90° C. |
| 5-methylthio-1,3,4-thiadiazole-2-carboxylic acid-allylamide | M.p.: 88° C. |
| 5-methylthio-1,3,4-thiadiazole-2-carboxylic acid-ethylamide | M.p.: 83° C. |
| 5-methylthio-1,3,4-thiadiazole-2-carboxylic acid-isopropylamide | M.p.: 101° C. |
| 5-methylthio-1,3,4-thiadiazole-2-carboxylic acid-(2-methoxyethyl)-amide | M.p.: 83° C. |
| 5-methylthio-1,3,4-thiadiazole-2-carboxylic acid-(3-methoxypropyl)-amide | M.p.: 57° C. |
| 5-methylthio-1,3,4thiadiazole-2-carboxylic acid-cyclopropylamide | M.p.: 130° C. |
| 5-methylthio-1,3,4-thiadiazole-2-carboxylic acid-N,N-trimethyleneamide | M.p.: 106° C. |

-continued

| Compound | Physical Constants |
|---|---|
| 5-butylthio-1,3,4-thiadiazole-2-carboxamide | M.p.: 165° C. |
| 5-hexylthio-1,3,4-thiadiazole-2-carboxamide | M.p.: 150° C. |
| 5-(2-methyl-2-propenylthio)-1,3,4-thiadiazole-2-carboxylic acid-2-propenylamide | $n_D^{20}$: 1.5793 |
| 5-(2-methyl-2-propenylthio)-1,3,4-thiadiazole-2-carboxylic acid-isopropylamide | M.p.: 69° C. |
| 5-(propenylthio)1,3,4-thiadiazole 2-(carboxylic acid amide | M.p.: 144° C. |
| 5-(2-propenylthio)-1,3,4-thiadiazole-carboxylic acid-methylamide | M.p.: 87° C. |
| 5-(2-propenylthio)-1,3,4-thiadiazole-2-carboxylic acid-ethylamide | M.p.: 70° C. |
| 5-(2-propenylthio)-1,3,4-thiadiazole-2-carboxylic acid-propylamide | M.p.: 65° C. |
| 5-(2-propenylthio)-1,3,4-thiadiazole-2-carboxylic acid-isopropylamide | M.p: 95° C. |
| 5-(2-propenylthio)-1,3,4-thiadiazole-2-carboxylic acid (2-propenylamide) | M.p.: 54° C. |
| 5-(2-propenylthio)-1,3,4-thiadiazole-2-carboxylic acid-ethylester | $n_D^{20}$: 1.5825 |
| 5-butylthio-1,3,4-thiadiazole-2-carboxylic acid-ethylester | $n_D^{20}$: 1.5540 |
| 5-butylthio-1,3,4-thiadiazole-2-carboxylic acid-methylamide | M.p.: 83° C. |
| 5-butylthio-1,3,4-thiadiazole-2-carboxylic acid-propylamide | M.p.: 52° C. |
| 5-butylthio-1,3,4-thiadiazole-2-carboxylic acid ethylamide | M.p.: 67° C. |
| 5-butylthio-1,3,4-thiadiazole-2-carboxylic acid-isopropylamide | M.p.: 79° C. |
| 5-isopropylthio-1,3,4-thiadiazole-2-carboxylic acid-butylamide | M.p.: 53° C. |
| 5-sec.-butylthio-1,3,4-thiadiazole-2-carboxylic acid-ethylester | $n_D^{20}$: 1.5527 |
| 5-sec.-butylthio-1,3,4-thiadiazole-2-carboxylic acid-methylamide | $n_D^{20}$: 1.5762 |
| 5-sec.-butylthio-1,3,4-thiadiazole-2-carboxylic acid-ethylamide | $n_D^{20}$: 1.5651 |
| 5-cyclohexylthio-1,3,4-thiadiazole-2-carboxamide | M.p.: 158° C. |
| 5-(2-propinylthio)-1,3,4-thiadiazole-2-carboxylic acid-amide | M.p.: 180° C. |
| 5-pentylthio-1,3,4-thiadiazole-2-carboxylic acid-methylamide | M.p.: 82° C. |
| 5-hexylthio-1,3,4-thiadiazole-2-carboxylic acid-methylamide | M.p.: 80° C. |
| 5-sec.-butylthio-1,3,4-thiadiazole-2-carboxylic acid-(2-methoxyethyl)-amide | $n_D^{20}$: 1.5585 |
| 5-sec.-butylthio-1,3,4-thiadiazole-2-carboxylic acid-cyclopropylamide | M.p.: 50° C. |
| 5-pentylthio-1,3,4-thiadiazole-2-carboxylic acid-isobutylamide | M.p.: 80° C. |
| 5-hexylthio-1,3,4-thiadiazole-2-carboxylic acid-propylamide | M.p.: 61° C. |
| 5-sec.-butylthio-1,3,4-thiadiazole-2-carboxylic acid-(3-methoxypropyl)-amide | $n_D^{20}$: 1.5566 |
| 5-pentylthio-1,3,4-thiadiazole-2-carboxylic acid-cyclopropylamide | M.p.: 87° C. |
| 5-(2-propinylthio)-1,3,4-thiadiazole-2-carboxylic acid-ethylester | M.p.: 57° C. |
| 5-pentylthio-1,3,4-thiadiazole-2-carboxylic acid-(2-propenyl)-amide | M.p.: 60° C. |
| 5-hexylthio-1,3,4-thiadiazole-2-carboxylic acid-(2-propenyl)-amide | M.p.: 90° C. |
| 5-hexylthio-1,3,4-thiadiazole-2-carboxylic acid-cyclopropylamide | M.p.: 54° C. |
| 5-hexylthio-1,3,4-thiadiazole-2-carboxylic acid-(2-methoxyethyl)-amide | M.p.: 52° C. |

These compounds are soluble in carboxylic acids, carboxylic amides, carboxylic acid esters and halogenated hydrocarbons. They are less soluble in hydrocarbons and insoluble in water.

EXAMPLES ILLUSTRATING USES AND ACTIVITIES

The following examples are furnished to illustrate the various uses and the superior fungicidal activity of the compounds of the invention.

EXAMPLE 14

Threshold concentration test for use of the compounds against *Pythium ultimum*

A 20% concentration of certain pulverulent active agents as listed below were mixed in uniform manner into a soil which had been heavily infested by *Pythium ultimum*. The thus treated soil was then placed into clay dishes of a capacity of 0.5 l earth. Without any intermediate time lapse 20 grain of garden peas (*Pisum sativum* L. convar. medullare Alef.) of the type "Wunder von Kelvedon" were then seeded into each of the clay dishes. After a cultivation period of three weeks at 20° to 24° C. in a hothouse the number of sound peas was determined and a root evaluation was carried out. The active agents amounts and results appear from the following table.

The root evaluation was carried out on a scale from 1 to 4 as follows:

4 = white roots without fungous necrosis;
3 = white roots, minor fungous necrosis;
2 = brown roots, already more pronounced fungous necrosis;
1 = heavy fungous necrosis, roots rotted.

| Active agent | Concentration of agent in mg/l soil | number of sound peas | root evaluation (1–4) |
|---|---|---|---|
| 5-methylsulfonyl-1,3,4-thiadiazole-2-carboxamide | 20 mg | 16 | 4 |
| | 40 mg | 18 | 4 |
| | 80 mg | 20 | 4 |
| 5-methylsulfonyl-1,3,4-thiadiazole-2-carbonitrile | 20 mg | 17 | 3 |
| | 40 mg | 16 | 4 |
| | 80 mg | 20 | 4 |
| 5-ethylsulfonyl-1,3,4-thiadiazole-2-carboxamide | 20 mg | 18 | 2 |
| | 40 mg | 18 | 4 |
| | 80 mg | 20 | 4 |
| 5-ethylsulfonyl-1,3,4-thiadiazole-2-carbonitrile | 20 mg | 19 | 2 |
| | 40 mg | 20 | 4 |
| | 80 mg | 20 | 4 |
| 5-ethylsulfinyl-1,3,4-thiadiazole-2-carboxamide | 20 mg | 15 | 2 |
| | 40 mg | 20 | 4 |
| | 80 mg | 20 | 4 |
| 5-isopropylsulfonyl-1,3,4-thiadiazole-2-carboxamide | 20 mg | 17 | 4 |
| | 40 mg | 18 | 4 |
| | 80 mg | 19 | 4 |
| 5-isopropylsulfonyl-1,3,4-thiadiazole-2-carbonitrile | 20 mg | 18 | 2 |
| | 40 mg | 20 | 4 |
| | 80 mg | 19 | 4 |
| 5-methylsulfonyl-1,3,4-thiadiazole-2-carboxylic acid-methylamide | 20 mg | 20 | 4 |
| | 40 mg | 18 | 4 |
| | 80 mg | 18 | 4 |
| 5-methylsulfonyl-1,3,4-thiadiazole-2-carboxylic acid-dimethylamide | 20 mg | 18 | 4 |
| | 40 mg | 20 | 4 |
| | 80 mg | 18 | 4 |
| 5-isobutylsulfonyl-1,3,4-thiadiazole-2-carboxamide | 20 mg | 15 | 1 |
| | 40 mg | 18 | 4 |
| | 80 mg | 18 | 4 |
| 5-ethylsulfonyl-1,3,4-thiadiazole-2-carboxylic acid-methylamide | 20 mg | 17 | 4 |
| | 40 mg | 15 | 4 |
| | 80 mg | 19 | 4 |
| 5-ethylsulfonyl-1,3,4-thiadiazole-2-carboxylic acid-dimethylamide | 20 mg | 13 | 4 |
| | 40 mg | 13 | 4 |
| | 80 mg | 15 | 4 |

| | Concentration of agent in mg/l soil | number of sound peas | root evaluation (1-4) |
|---|---|---|---|
| 5-propylsulfonyl-1,3,4-thiadiazole-2-carboxamide | 20 mg | 12 | 1 |
| | 40 mg | 19 | 4 |
| | 80 mg | 17 | 4 |
| 5-propylsulfonyl-1,3,4-thiadiazole-2-carboxylic acid-methylamide | 20 mg | 19 | 4 |
| | 40 mg | 16 | 4 |
| | 80 mg | 15 | 4 |
| 5-ethylsulfonyl-1,3,4-thiadiazole-2-carboxylic acid-butylamide | 20 mg | 8 | 1 |
| | 40 mg | 16 | 4 |
| | 80 mg | 20 | 4 |
| 5-ethylsulfonyl-1,3,4-thiadiazole-2-carboxylic acid-ethylamide | 20 mg | 15 | 4 |
| | 40 mg | 16 | 4 |
| | 80 mg | 16 | 4 |
| 5-methylsulfinyl-1,3,4-thiadiazole-2-carbonitrile | 20 mg | 19 | 4 |
| | 40 mg | 20 | 4 |
| | 80 mg | 20 | 4 |
| 5-ethylsulfinyl-1,3,4-thiadiazole-2-carbonitrile | 20 mg | 20 | 4 |
| | 40 mg | 19 | 4 |
| | 80 mg | 19 | 4 |
| 5-propylsulfinyl-1,3,4-thiadiazole-2-carbonitrile | 20 mg | 9 | 1 |
| | 40 mg | 16 | 4 |
| | 80 mg | 18 | 4 |
| 5-isopropylsulfinyl-1,3,4-thiadiazole-2-carbonitrile | 20 mg | 17 | 3 |
| | 40 mg | 17 | 4 |
| | 80 mg | 19 | 4 |
| 5-butylsulfinyl-1,3,4-thiadiazole-2-carbontrile | 20 mg | 18 | 4 |
| | 40 mg | 18 | 4 |
| | 80 mg | 20 | 4 |
| 5-ethylsulfonyl-1,3,4-thiadiazole-2-carboxylic acid-N,N-trimethylenamide | 20 mg | 20 | 4 |
| | 40 mg | 19 | 4 |
| | 80 mg | 20 | 4 |
| 5-propylsulfonyl-1,3,4-thiadiazole-2-carboxylic acid-N,N-trimethyleneamide | 20 mg | 6 | 1 |
| | 40 mg | 19 | 4 |
| | 80 mg | 18 | 4 |
| 5-propylsulfonyl-1,3,4-thiadiazole-2-carboxylic acid-(3-chloropropyl)-amide | 20 mg | 10 | 1 |
| | 40 mg | 19 | 3 |
| | 80 mg | 19 | 4 |
| 5-propylsulfinyl-1,3,4-thiadiazole-2-carboxylic acid-dimethylamide | 20 mg | 12 | 1 |
| | 40 mg | 18 | 4 |
| | 80 mg | 19 | 4 |
| 5-propylsulfonyl-1,3,4-thiadiazole-2-carboxylic acid-dimethylamide | 20 mg | 17 | 2 |
| | 40 mg | 20 | 4 |
| | 80 mg | 19 | 4 |
| 5-methylsulfonyl-1,3,4-thiadiazole-2-carboxylic acid-allylamide | 20 mg | 19 | 4 |
| | 40 mg | 18 | 4 |
| | 80 mg | 18 | 4 |
| 5-methylsulfinyl-1,3,4-thiadiazole-2-carboxylic acid-allylamide | 20 mg | 20 | 4 |
| | 40 mg | 19 | 4 |
| | 80 mg | 18 | 4 |
| 5-ethylsulfonyl-1,3,4-thiadiazole-2-carboxylic acid-tetramethyleneamide | 20 mg | 14 | 2 |
| | 40 mg | 20 | 4 |
| | 80 mg | 20 | 4 |
| 5-propylsulfonyl-1,3,4-thiadiazole-2-carboxylic acid-isopropylamide | 20 mg | 9 | 1 |
| | 40 mg | 20 | 4 |
| | 80 mg | 18 | 4 |
| 5-propylsulfinyl-1,3,4-thiadiazole-2-carboxylic acid-allylamide | 20 mg | 15 | 2 |
| | 40 mg | 19 | 4 |
| | 80 mg | 19 | 4 |
| 5-methylsulfonyl-1,3,4-thiadiazole-2-carboxylic acid-(3-methoxypropyl)-amide | 20 mg | 9 | 1 |
| | 40 mg | 20 | 4 |
| | 80 mg | 19 | 4 |
| 5-methylsulfinyl-1,3,4-thiadiazole-2-carboxylic acid-ethylamide | 20 mg | 18 | 2 |
| | 40 mg | 18 | 4 |
| | 80 mg | 19 | 4 |
| 5-methylsulfinyl-1,3,4-thiadiazole-2-carboxylic acid-isopropylamide | 20 mg | 19 | 4 |
| | 40 mg | 19 | 4 |
| | 80 mg | 20 | 4 |
| 5-methylsulfonyl-1,3,4-thiadiazole-2-carboxylic acid-cyclopropylamide | 20 mg | 13 | 1 |
| | 40 mg | 20 | 4 |
| | 80 mg | 20 | 4 |
| 5-methylsulfinyl-1,3,4-thiadiazole-2-carboxylic acid-cyclopropylamide | 20 mg | 15 | 1 |
| | 40 mg | 20 | 4 |
| | 80 mg | 20 | 4 |
| 5-methylsulfonyl-1,3,4-thiadiazole-2-carboxylic acid-N,N-trimethyleneamide | 20 mg | 19 | 4 |
| | 40 mg | 20 | 4 |
| | 80 mg | 20 | 4 |
| 5-methylsulfinyl-1,3,4-thiadiazole-2-carboxylic acid-N,N-trimethyleneamide | 20 mg | 12 | 2 |
| | 40 mg | 16 | 4 |
| | 80 mg | 19 | 4 |
| 5-butylsulfonyl-1,3,4-thiadiazole-2-carboxamide | 20 mg | 11 | 1 |
| | 40 mg | 20 | 4 |
| | 80 mg | 18 | 4 |
| 5-butylsulfinyl-1,3,4-thiadiazole-2-carboxamide | 20 mg | 10 | 1 |
| | 40 mg | 15 | 4 |
| | 80 mg | 19 | 4 |
| 5-methylsulfonyl-1,3,4-thiadiazole-2-carboxylic acid-ethylamide | 20 mg | 15 | 4 |
| | 40 mg | 15 | 4 |
| | 80 mg | 15 | 4 |
| 5-methylsulfonyl-1,3,4-thiadiazole-2-carboxylic acid-isopropylamide | 20 mg | 15 | 4 |
| | 40 mg | 18 | 4 |
| | 80 mg | 15 | 4 |
| 5-methylsulfonyl-1,3,4-thiadiazole-2-carboxylic acid-propylamide | 20 mg | 15 | 4 |
| | 40 mg | 15 | 4 |
| | 80 mg | 15 | 4 |
| 5-methylsulfonyl-1,3,4-thiadiazole-2-carboxylic acid-butylamide | 20 mg | 14 | 2 |
| | 40 mg | 15 | 4 |
| | 80 mg | 16 | 4 |
| 5-methylsulfinyl-1,3,4-thiadiazole-2-carboxylic acid-propylamide | 20 mg | 14 | 4 |
| | 40 mg | 15 | 4 |
| | 80 mg | 15 | 4 |
| 5-methylsulfinyl-1,3,4-thiadiazole-2-carboxylic acid-butylamide | 20 mg | 12 | 2 |
| | 40 mg | 15 | 4 |
| | 80 mg | 17 | 4 |
| 5-propylsulfonyl-1,3,4-thiadiazole-2-carboxylic acid-ethylamide | 20 mg | 14 | 3 |
| | 40 mg | 14 | 4 |
| | 80 mg | 14 | 4 |
| 5-propylsulfonyl-1,3,4-thiadiazole-2-carboxylic acid-propylamide | 20 mg | 10 | 1 |
| | 40 mg | 16 | 4 |
| | 80 mg | 16 | 4 |
| 5-propylsulfonyl-1,3,4-thiadiazole-2-carboxylic acid-allylamide | 20 mg | 13 | 3 |
| | 40 mg | 15 | 4 |
| | 80 mg | 15 | 4 |
| 5-ethylsulfonyl-1,3,4-thiadiazole-2-carboxylic acid-isopropylamide | 20 mg | 16 | 3 |
| | 40 mg | 15 | 3 |
| | 80 mg | 16 | 4 |
| 5-ethylsulfonyl-1,3,4-thiadiazole-2-carboxylic acid-allylamide | 20 mg | 11 | 1 |
| | 40 mg | 17 | 4 |
| | 80 mg | 16 | 4 |
| 5-ethylsulfonyl-1,3,4-thiadiazole-2-carboxylic acid-(2-methoxyethyl)-amide | 20 mg | 13 | 1 |
| | 40 mg | 16 | 4 |
| | 80 mg | 16 | 4 |
| 5-ethylsulfonyl-1,3,4-thiadiazole-2-carboxylic acid-(3-methoxypropyl)-amide | 20 mg | 11 | 1 |
| | 40 mg | 18 | 4 |
| | 80 mg | 17 | 4 |
| Comparison compounds | | | |
| Manganese ethylene-1,2-bis-dithiocarbamate | 20 mg | 1 | 1 |
| | 40 mg | 4 | 1 |
| | 80 mg | 11 | 1 |
| N-trichloromethylmercapto-tetrahydro-phthalimide | 20 mg | 1 | 1 |
| | 40 mg | 2 | 1 |
| | 80 mg | 8 | 2 |
| Control I. (3 times repeated) | | | |
| Infested soil; no treatment | — | 1 | 1 |
| | — | 0 | 1 |
| | — | 0 | 1 |
| Control II. (3 times repeated) | | | |
| Humidified soil | — | 18 | 4 |
| | — | 20 | 4 |
| | — | 17 | 4 |

EXAMPLE 15

Threshold concentration test in case of *Fusarium avenaceum*

A 20% pulverulent active agent of the type further identified in the table below was mixed in uniform manner with a soil which had been heavily infested with *Fusarium avenaceum*. The thus treated soil was then placed into clay dishes of a capacity of 0.5 l of earth. Each dish was seeded without any intervening time with 20 grains of garden peas (*Pisum sativum* L. convar. medullare Alef.) of the type "Wunder von Kelvedon".

After a cultivation time of 18 days at 20° to 24° C. in a hot house the number of sound peas was determined and a root evaluation was carried out. The active agents employed, the amounts and results appear from the following table.

The root evaluation was carried out on a scale from 1 to 4 as follows:
4 = white roots without fungous necroses
3 = white roots with minor fungous necroses
2 = brown roots already more pronounced fungous necroses '1 = heavy fungous necroses with roots rotted.

| Active agent | Concentration of agent in mg/l soil | number of sound peas | root evaluation (1-4) |
|---|---|---|---|
| 5-methylsulfinyl-1,3,4-thiadiazole-2-carbonitrile | 25 mg | 20 | 4 |
| | 50 mg | 18 | 4 |
| | 100 mg | 19 | 4 |
| 5-methylsulfonyl-1,3,4-thiadiazole-carbonitrile | 25 mg | 18 | 4 |
| | 50 mg | 17 | 4 |
| | 100 mg | 19 | 4 |
| 5-ethylsulfinyl-1,3,4-thiadiazole-2-carbonitrile | 25 mg | 19 | 4 |
| | 50 mg | 20 | 4 |
| | 100 mg | 20 | 4 |
| 5-ethylsulfonyl-1,3,4-thiadiazole-2-carbonitrile | 25 mg | 18 | 4 |
| | 50 mg | 20 | 4 |
| | 100 mg | 20 | 4 |
| 5-propylsulfinyl-1,3,4-thiadiazole-2-carbonitrile | 25 mg | 19 | 4 |
| | 50 mg | 20 | 4 |
| | 100 mg | 19 | 4 |
| 5-propylsulfonyl-1,3,4-thiadiazole-2-carbonitrile | 25 mg | 18 | 4 |
| | 50 mg | 20 | 4 |
| | 100 mg | 20 | 4 |
| 5-isopropylsulfinyl-1,3,4-thiadiazole-2-carbonitrile | 25 mg | 18 | 4 |
| | 50 mg | 19 | 4 |
| | 100 mg | 18 | 4 |
| 5-isopropylsulfonyl-1,3,4-thiadiazole-2-carbonitrile | 25 mg | 20 | 4 |
| | 50 mg | 20 | 4 |
| | 100 mg | 19 | 4 |
| 5-butylsulfinyl-1,3,4-thiadiazole-2-carbonitrile | 25 mg | 19 | 4 |
| | 50 mg | 19 | 4 |
| | 100 mg | 19 | 4 |
| 5-butylsulfonyl-1,3,4-thiadiazole-2-carbonitrile | 25 mg | 18 | 4 |
| | 50 mg | 20 | 4 |
| | 100 mg | 20 | 4 |
| 5-sec.-butylsulfonyl-1,3,4-thiadiazole-2-carbonitrile | 25 mg | 20 | 4 |
| | 50 mg | 19 | 4 |
| | 100 mg | 20 | 4 |
| 5-isobutylsulfonyl-1,3,4-thiadiazole-2-carbonitrile | 25 mg | 19 | 4 |
| | 50 mg | 20 | 4 |
| | 100 mg | 19 | 4 |
| 5-pentylsulfonyl-1,3,4-thiadiazole-2-carbonitrile | 25 mg | 20 | 4 |
| | 50 mg | 20 | 4 |
| | 100 mg | 19 | 4 |
| 5-hexylsulfonyl-1,3,4-thiadiazole-2-carbonitrile | 25 mg | 19 | 4 |
| | 50 mg | 19 | 4 |
| | 100 mg | 19 | 4 |
| 5-pentylsulfonyl-1,3,4-thiadiazole-2-carboxamide | 25 mg | 9 | 2 |
| | 50 mg | 16 | 3 |
| | 100 mg | 18 | 4 |
| 5-hexylsulfonyl-1,3,4-thiadiazole-2-carboxamide | 25 mg | 7 | 1 |
| | 50 mg | 12 | 2 |
| | 100 mg | 15 | 3 |
| 5-propylsulfonyl-1,3,4-thiadiazole-2-carboxylic acid-N,N-trimethyleneamide | 25 mg | 11 | 2 |
| | 50 mg | 17 | 3 |
| | 100 mg | 17 | 3 |
| 5-n-butylsulfonyl-1,3,4-thiadiazole-2-carboxylic acid-N,N-trimethyleneamide | 25 mg | 5 | 1 |
| | 50 mg | 13 | 2 |
| | 100 mg | 18 | 3 |
| 5-propylsulfinyl-1,3,4-thiadiazole-2-carboxylic acid-isopropylamide | 25 mg | 9 | 3 |
| | 50 mg | 13 | 4 |
| | 100 mg | 16 | 4 |
| 5-methylsulfinyl-1,3,4-thiadiazole-2-carboxylic acid-(2-chlorobenzyleamide) | 25 mg | 7 | 2 |
| | 50 mg | 11 | 3 |
| | 100 mg | 18 | 4 |
| 5-butylsulfonyl-1,3,4-thiadiazole-2-carboxamide | 25 mg | 15 | 2 |
| | 50 mg | 12 | 3 |
| | 100 mg | 16 | 4 |
| 5-propylsulfinyl-1,3,4-thiadiazole-2-carboxylic acid-sec.-butylamide | 25 mg | 9 | 1 |
| | 50 mg | 17 | 4 |
| | 100 mg | 17 | 4 |
| 5-propylsulfonyl-1,3,4-thiadiazole-2-carboxylic acid-isopropylamide | 25 mg | 14 | 2 |
| | 50 mg | 16 | 3 |
| | 100 mg | 17 | 4 |
| 5-propylsulfonyl-1,3,4-thiadiazole-2-carboxylic acid-butylamide | 25 mg | 9 | 1 |
| | 50 mg | 16 | 3 |
| | 100 mg | 17 | 4 |
| Comparison compound: | | | |
| 3-trichloromethyl-5-ethoxy-1,2,4-thiadiazole | 25 mg | 0 | 1 |
| | 50 mg | 0 | 1 |
| | 100 mg | 0 | 1 |
| Manganese-ethylene-1,2,-bis-dithiocarbamate | 25 mg | 0 | 1 |
| | 50 mg | 0 | 1 |
| | 100 mg | 12 | 1 |
| Control I. (3 times repeated) Infested soil; no treatment | — | 0 | 1 |
| | — | 0 | 1 |
| | — | 0 | 1 |
| Control II. (3 times repeated) Humidified soil | — | 18 | 4 |
| | — | 20 | 4 |
| | — | 19 | 4 |

EXAMPLE 16

Inhibition of fungus in a nutrient solution 20 ml of a nutrient solution of grape juice and water (1:1) were filled into a glass vial of a 100 ml capacity and were mixed with the pulverulent active agents which appear from the subsequent table. Thereafter, the solution was inoculated with conidia (spores) of the test fungi.

After an incubation time of 6 days at 21° to 23° C. the fungus development on the surface of the nutrient solution was evaluated. The test fungi used were the following: *Penicillium digitatum, Botrytis cinerea, Alternaria solani, Fusarium avenaceum.*

The evaluation was carried out at a scale from 0 to 5 as follows:
0 = no fungus growth;
1 = isolated fungus colonies on the surface;
2 = 5 to 10% of the surface covered by the fungus turf;
3 = 10 to 30% of the surface covered by the fungus turf;
4 = 30 to 60% of the surface covered by the fungus turf;
5 = 60 to 100% of the surface covered by the fungus turf.

The active agent concentrations in the nutrient solution and the results appear from the following table.

| Active agent | Concentration of agent in the nutrient solution | Penicillium digitatum | Botrytis cinerea | Alternaria solani | Fusarium avenaceum |
|---|---|---|---|---|---|
| 5-methylsulfonyl-1,3-4- | 0.002% | 1 | 1 | 0 | 0 |

-continued

| Active agent | Concentration of agent in the nutrient solution | Penicillium digitatum | Botrytis cinerea | Alternaria solani | Fusarium avenaceum |
|---|---|---|---|---|---|
| thiadiazole-2-carbonitrile | 0.004% | 0 | 0 | 0 | 0 |
| 5-ethylsulfonyl-1,3,4-thiadiazole-2-carbonitrile | 0.002% | 0 | 1 | 0 | 0 |
| | 0.004% | 0 | 0 | 0 | 0 |
| 5-isopropylsulfonyl-1,3,4-thiadiazole-2-carbonitrile | 0.002% | 0 | 1 | 0 | 0 |
| | 0.004% | 0 | 0 | 0 | 0 |
| 5-methylsulfonyl-1,3,4-thiadiazole-2-carboxylic acid-methylester | 0.002% | 1 | 1 | 1 | 0 |
| | 0.004% | 0 | 0 | 0 | 0 |
| 5-ethylsulfonyl-1,3,4-thiadiazole-2-carboxylic acid-ethylester | 0.002% | 1 | 2 | 0 | 1 |
| | 0.004% | 0 | 0 | 0 | 0 |
| 5-ethylsulfonyl-1,3,4-thiadiazole-2-carboxylic acid-butylamide | 0.002% | 1 | 2 | 1 | 1 |
| | 0.004% | 0 | 0 | 0 | 0 |
| 5-isobutylsulfonyl-1,3,4-thiadiazole-2-carboxamide | 0.002% | 1 | 2 | 0 | 2 |
| | 0.004% | 0 | 1 | 0 | 0 |
| N-trichloromethylmercapto-phthalimide | 0.002% | 4 | 4 | 4 | 4 |
| | 0.004% | 4 | 3 | 4 | 4 |
| N-trichloromethylmercapto-tetrahydro-phthalimide | 0.002% | 4 | 4 | 4 | 4 |
| | 0.004% | 4 | 4 | 4 | 4 |
| Tetrachloroisophthalo-dinitrile | 0.002% | 3 | 5 | 5 | 4 |
| | 0.004% | 2 | 4 | 5 | 3 |
| Control: untreated nutrient solution | — | 5 | 5 | 5 | 5 |

EXAMPLE 17

Threshold concentration test with root gall nematodes (*Meloidogyne sp.*)

20% concentration pulverulent active agents as listed in the table below were mixed in a uniform manner with a soil which had been heavily infested by root gall nematodes. After waiting for 3 days the treated soil was placed in two clay dishes of a capacity of 0.5 liter. 10 grain of cucumber seeds of the type "Guntruud" were placed into each dish.

Thereafter, the contents of the dishes were permitted to develop at a temperature of 24° to 27° C. for a time of 28 days in a hothouse. The cucumber roots were then washed out and were examined in a water bath regarding nematode infestation. The reduction of the infestation by the active agents as compared with untreated control material was determined in percentages.

The active agents amounts and reduction of infestation appear from the following table.

The nematocidal activity was calculated by the formula $$(A-B)/A \cdot 100$$

In this formula
A = the infestation in the untreated control material and
B = the infestation after treatment.

| Active agent | Percentage reduction of infestation at the following agent concentrations given in mg per liter soil | | |
|---|---|---|---|
| | 200 mg | 100 mg | 50 mg |
| 5-methylsulfonyl-1,3,4-thiadiazole-2-carbonitrile | 96% | 88% | 71% |
| 5-methylthio-1,3,4-thiadiazole-2-carbonitrile | 100% | 99% | 95% |

EXAMPLE 18

Treatment of barley seeds infested with Helminthosporium gram

Barley seeds which all had a natural infestation by Helminthosporium gram were seeded in plant pots filled with earth and left to germination at a temperature below +16° C. Some of the seeds had not been treated, others had been treated with the active agents listed in the table. After emergence, the plants were subjected to illumination for 12 hours per day. After about 5 weeks the infested plants were counted and the total number of plants for each test were also counted. The active agents tested were used as pulverulent compositions.

The fungicidal activity was calculated as follows:

$$100 - \frac{100 \cdot \text{infestation in treated plants}}{\text{infestation in untreated plants}} = \% \text{ activity}$$

| Active agent | Amount of active agent in grams per 100 kg | % activity |
|---|---|---|
| 5-methylsulfonyl-1,3,4-thiadiazole-2-carboxamide | 10 | 95 |
| | 20 | 100 |
| | 50 | 100 |
| 5-ethylsulfonyl-1,3,4-thiadiazole-2-carboxamide | 10 | 97 |
| | 20 | 100 |
| | 50 | 100 |
| 5-ethylsulfinyl-1,3,4-thiadiazole-2-carboxamide | 10 | 99 |
| | 20 | 100 |
| | 50 | 100 |
| 5-isopropylsulfonyl-1,3,4-thiadiazole-2-carbonitrile | 10 | — |
| | 20 | 86 |
| | 50 | 97 |
| 5-methylsulfonyl-1,3,4-thiadiazole-2-carboxylic acid-methylamide | 10 | — |
| | 20 | 99 |
| | 50 | 100 |
| 5-methylsulfonyl-1,3,4-thiadiazole-2-carboxylic acid-dimethylamide | 10 | — |
| | 20 | 87 |
| | 50 | 98 |
| 5-isobutylsulfonyl-1,3,4-thiadiazole-2-carboxamide | 10 | — |
| | 20 | 60 |

-continued

| | Amount of active agent in grams per 100 kg | % activity |
|---|---|---|
| | 50 | 87 |
| 5-ethylsulfonyl-1,3,4- | 10 | — |
| thiadiazole-2-carboxylic | 20 | 91 |
| acid-methylamide | 50 | 97 |
| 5-ethylsulfonyl-1,3,4- | 10 | — |
| thiadiazole-2-carboxylic | 20 | 94 |
| acid-dimethylamide | 50 | 100 |
| 5-ethylsulfonyl-1,3,4- | 10 | — |
| thiadiazole-2-carboxylic | 20 | 100 |
| acid-ethylamide | 50 | 100 |
| 5-ethylsulfonyl-1,3,4- | 10 | — |
| thiadiazole-2-carboxylic | 20 | — |
| acid-propylamide | 50 | 92 |
| 5-ethylsulfonyl-1,3,4- | 10 | — |
| thiadiazole-2-carboxylic | 20 | 100 |
| acid-(N-butyl-N-methyl)-amide | 50 | 100 |
| 5-ethylsulfonyl-1,3,4- | 10 | 100 |
| thiadiazole-2-carboxylic | 20 | 99 |
| acid-(2-methoxyethyl)-amide | 50 | 100 |
| 5-ethylsulfonyl-1,3,4-thia- | 10 | 99 |
| diazole-2-carboxylic acid- | 20 | 99 |
| (3-methoxypropyl)-amide | 50 | 100 |
| 5-ethylsulfonyl-1,3,4- | 10 | 95 |
| thiadiazole-2-carboxylic | 20 | 98 |
| acid-isopropyl-amide | 50 | 100 |
| 5-ethylsulfonyl-1,3,4- | 10 | 100 |
| thiadiazole-2-carboxylic | 20 | 100 |
| acid-allylamide | 50 | 100 |
| 5-ethylsulfonyl-1,3,4- | 10 | 98 |
| thiadiazole-2-carboxylic | 20 | 100 |
| acid-N,N-tetramethyleneamide | 50 | 99 |
| 5-ethylsulfonyl-1,3,4-thia- | 10 | 99 |
| diazole-2-carboxylic acid- | 20 | 100 |
| (N,N-3-oxapentamethyleneamide) | 50 | 100 |
| 5-ethylsulfonyl-1,3,4-thia- | 10 | — |
| diazole-2-carboxylic acid- | 20 | — |
| cyclooctylamide | 50 | 98 |
| 5-propylsulfinyl-1,3,4-thia- | 10 | — |
| diazole-2-carbonitrile | 20 | 87 |
| | 50 | 99 |
| 5-ethylsulfinyl-1,3,4-thia- | 10 | 98 |
| diazole-2-carbonitrile | 20 | 100 |
| | 50 | 100 |
| 5-methylsulfonyl-1,3,4-thia- | 10 | — |
| diazole-2-carboxylic acid- | 20 | — |
| ethylamide | 50 | 93 |
| 5-methylsulfonyl-1,3,4-thia- | 10 | — |
| diazole-2-carboxylic acid- | 20 | — |
| isopropylamide | 50 | 90 |
| 5-methylsulfonyl-1,3,4-thia- | 10 | — |
| diazole-2-carboxylic acid- | 20 | — |
| propylamide | 50 | 93 |
| 5-methylsulfonyl-1,3,4-thia- | 10 | — |
| diazole-2-carboxylic acid- | 20 | — |
| butylamide | 50 | 90 |
| 5-methylsulfinyl-1,3,4-thia- | 10 | 75 |
| diazole-2-carboxylic acid- | 20 | 98 |
| propylamide | 50 | 100 |
| 5-methylsulfinyl-1,3,4-thia- | 10 | 67 |
| diazole-2-carboxylic acid- | 20 | 97 |
| butylamide | 50 | 100 |
| 5-sec.-butylsulfonyl-1,3,4-thia- | 10 | — |
| diazole-2-carboxamide | 20 | — |
| | 50 | 97 |
| 5-methylsulfinyl-1,3,4-thia- | 10 | 94 |
| diazole-2-carboxylic acid- | 20 | 99 |
| allylamide | 50 | 100 |
| 5-methylsulfonyl-1,3,4-thia- | 10 | — |
| diazole-2-carboxylic acid- | 20 | — |
| allylamide | 50 | 100 |
| 5-propylsulfinyl-1,3,4-thia- | 10 | — |
| diazole-2-carboxylic acid- | 20 | — |
| ethylamide | 50 | 94 |
| 5-propylsulfinyl-1,3,4-thia- | 10 | — |
| diazole-2-carboxylic acid- | 20 | — |
| propylamide | 50 | 94 |
| 5-propylsulfinyl-1,3,4-thia- | 10 | — |
| diazole-2-carboxylic acid- | 20 | — |
| allylamide | 50 | 96 |
| 5-propylsulfinyl-1,3,4-thia- | 10 | — |
| diazole-2-carboxylic acid- | 20 | — |
| isopropylamide | 50 | 100 |
| 5-methylsulfinyl-1,3,4-thia- | 10 | 75 |
| diazole-2-carboxylic acid- | 20 | 97 |
| (2-methoxyethyl)-amide | 50 | 100 |
| 5-methylsulfonyl-1,3,4-thia- | 10 | — |
| diazole-2-carboxylic acid- | 20 | 92 |
| (2-methoxyethyl)-amide | 50 | 100 |
| 5-methylsulfinyl-1,3,4- | 10 | 98 |
| thiadiazole-2-carboxylic | 20 | 99 |
| acid-ethylamide | 50 | 100 |
| 5-methylsulfinyl-1,3,4-thia- | 10 | — |
| diazole-2-carboxylic acid- | 20 | 96 |
| isopropylamide | 50 | 100 |
| 5-methylsulfinyl-1,3,4-thia- | 10 | 72 |
| diazole-2-carboxylic acid- | 20 | 98 |
| cyclopropylamide | 50 | 99 |
| 5-methylsulfinyl-1,3,4-thia- | 10 | — |
| diazole-2-carboxylic acid- | 20 | 95 |
| N,N-trimethyleneamide | 50 | 100 |
| 5-propylsulfinyl-1,3,4-thia- | 10 | — |
| diazole-2-carboxylic acid- | 20 | — |
| dimethylamide | 50 | 93 |
| 5-butylsulfinyl-1,3,4-thia- | 10 | — |
| diazole-2-carboxylic acid- | 20 | — |
| dimethylamide | 50 | 100 |
| 5-propylsulfinyl-1,3,4-thia- | 10 | — |
| diazole-2-carboxylic acid- | 20 | — |
| sec.-butylamide | 50 | 94 |
| 5-propylsulfinyl-1,3,4-thia- | 10 | — |
| diazole-2-carboxylic acid- | 20 | — |
| dimethylamide | 50 | 100 |
| 5-methylsulfinyl-1,3,4-thia- | 10 | — |
| diadiazole-2-carbonitrile | 20 | — |
| | 50 | 94 |
| 5-methylsulfinyl-1,3,4-thia- | 10 | — |
| diazole-2-carboxamide | 20 | — |
| | 50 | 100 |
| 5-isopropylsulfinyl-1,3,4-thia- | 10 | — |
| diazole-2-carboxamide | 20 | — |
| | 50 | 100 |
| 5-isopropylsulfinyl-1,3,4-thia- | 10 | — |
| diazole-2-carbonitrile | 20 | — |
| | 50 | 93 |
| Comparison compound | | |
| Methoxyethyl-Hg—silicate | 0.2 | 63 |
| | 0.5 | 91 |
| | 1.0 | 98 |

EXAMPLE 19

Treatment of oat seeds infested with *Tilletia caries.*

Oat seeds were contaminated with 3 g of the spores of the stinking smuts (bunt) (*Tilletia caries*) per kg of seed material. Both untreated and treated grains were then pressed with their hairy end into Petri dishes filled with moist loam and were incubated at temperatures below 12° C. for 3 days. The grains were subsequently removed and the Petri dishes were further incubated with the remaining smut spores at about 12° C. After 10 days the spores were examined regarding germination. The active agents were employed in the form of pulverulent compositions.

The fungicidal activity was calculated on the basis of the following formula:

$$100 - \frac{100 \cdot \text{percentage of germination in treated grains}}{\text{percentage of germination in untreated grains}} = \% \text{ activity}$$

| Active agent | Amount of active agent in grams per 100 kg | % activity |
|---|---|---|
| 5-ethylsulfonyl-1,3,4-thiadiazole-2-carboxamide | 5 | 87 |
|  | 10 | 93 |
|  | 20 | 100 |
| 5-ethylsulfinyl-1,3,4-thiadiazole-2-carboxamide | 5 | 78 |
|  | 10 | 96 |
|  | 20 | 100 |
| 5-methylsulfonyl-1,3,4-thiadiazole-2-carboxylic acid-cyclohexyl-methylamide | 5 | 86 |
|  | 10 | 99 |
|  | 20 | 100 |
| 5-ethylsulfonyl-1,3,4-thiadiazole-2-carboxylic acid-methylamide | 10 | 100 |
|  | 20 | 100 |
|  | 50 | 100 |
| 5-ethylsulfonyl-1,3,4-thiadiazole-2-carboxylic acid-dimethylamide | 10 | 100 |
|  | 20 | 100 |
|  | 50 | 100 |
| 5-propylsulfonyl-1,3,4-thiadiazole-2-carboxamide | 10 | 100 |
|  | 20 | 100 |
|  | 50 | 100 |
| 5-propylsulfonyl-1,3,4-thiadiazole-2-carboxylic acid-methylamide | 10 | 99.5 |
|  | 20 | 99.5 |
|  | 50 | 100 |
| 5-ethylsulfonyl-1,3,4-thiadiazole-2-carboxylic acid-butylamide | 10 | 100 |
|  | 20 | 100 |
|  | 50 | 100 |
| 5-ethylsulfonyl-1,3,4-thiadiazole-2-carboxylic acid-cyclopropylamide | 10 | 85 |
|  | 20 | 100 |
|  | 50 | 100 |
| 5-ethylsulfonyl-1,3,4-thiadiazole-2-carboxylic acid-ethylamide | 10 | 99.3 |
|  | 20 | 100 |
|  | 50 | 100 |
| 5-ethylsulfonyl-1,3,4-thiadiazole-2-carboxylic acid-propylamide | 10 | 100 |
|  | 20 | 100 |
|  | 50 | 100 |
| 5-ethylsulfonyl-1,3,4-thiadiazole-2-carboxylic acid-(N-butyl-N-methyl)-amide | 10 | 98 |
|  | 20 | 100 |
|  | 50 | 100 |
| 5-ethylsulfonyl)-1,3,4-thiadiazole-2-carboxylic acid-(2-methoxyethyl)-amide | 10 | 100 |
|  | 20 | 100 |
|  | 50 | 100 |
| 5-ethylsulfonyl-1,3,4-thiadiazole-2-carboxylic acid-(3-methoxypropyl)-amide | 10 | 100 |
|  | 20 | 100 |
|  | 50 | 100 |
| 5-ethylsulfonyl-1,3,4-thiadiazole-2-carboxylic acid-isopropyl-amide | 10 | 100 |
|  | 20 | 100 |
|  | 50 | 100 |
| 5-ethylsulfonyl-1,3,4-thiadiazole-2-carboxylic acid-allylamide | 10 | 100 |
|  | 20 | 100 |
|  | 50 | 100 |
| 5-ethylsulfonyl-1,3,4-thiadiazole-2-carboxylic acid-octylamide | 10 | 91 |
|  | 20 | 93 |
|  | 50 | 98 |
| 5-ethylsulfonyl-1,3,4-thiadiazole-2-carboxylic acid-N,N-tetramethyleneamide | 10 | 100 |
|  | 20 | 100 |
|  | 50 | 100 |
| 5-ethylsulfonyl-1,3,4-thiadiazole-2-carboxylic acid-(N,N-3-oxapentamethyleneamide | 10 | — |
|  | 20 | — |
|  | 50 | 100 |
| 5-ethylsulfonyl-1,3,4-thiadiazole-2-carboxylic acid-cyclooctylamide | 10 | 100 |
|  | 20 | 100 |
|  | 50 | 100 |
| 5-propylsulfonyl-1,3,4-thiadiazole-2-carbonitrile | 10 | 99 |
|  | 20 | 100 |
|  | 50 | 100 |
| 5-propylsulfinyl-1,3,4-thiadiazole-2-carbonitrile | 10 | 99 |
|  | 20 | 100 |
|  | 50 | 100 |
| 5-ethylsulfinyl-1,3,4-thiadiazole-2-carbonitrile | 10 | 99.8 |
|  | 20 | 100 |
|  | 50 | 100 |
| 5-methylsulfonyl-1,3,4-thiadiazole-2-carboxylic acid-ethylamide | 10 | 99.2 |
|  | 20 | 99.2 |
|  | 50 | 98 |
| 5-methylsulfonyl-1,3,4-thiadiazole-2-carboxylic acid-isopropylamide | 10 | 100 |
|  | 20 | 100 |
|  | 50 | 100 |
| 5-methylsulfonyl-1,3,4-thiadiazole-2-carboxylic acid-propylamide | 10 | 99.5 |
|  | 20 | 100 |
|  | 50 | 100 |
| 5-methylsulfonyl-1,3,4-thiadiazole-2-carboxylic acid-butylamide | 10 | 99.2 |
|  | 20 | 100 |
|  | 50 | 100 |
| 5-methylsulfinyl-1,3,4-thiadiazole-2-carboxylic acid-propylamide | 10 | 99 |
|  | 20 | 100 |
|  | 50 | 100 |
| 5-methylsulfinyl-1,3,4-thiadiazole-2-carboxylic acid-butylamide | 10 | 99 |
|  | 20 | 99.8 |
|  | 50 | 100 |
| 5-propylsulfonyl-1,3,4-thiadiazole-2-carboxylic acid-ethylamide | 10 | 99.3 |
|  | 20 | 99.8 |
|  | 50 | 100 |
| 5-propylsulfonyl-1,3,4-thiadiazole-2-carboxylic acid-propylamide | 10 | 99.5 |
|  | 20 | 99.7 |
|  | 50 | 100 |
| 5-propylsulfonyl-1,3,4-thiadiazole-2-carboxylic acid-allylamide | 10 | 99.3 |
|  | 20 | 99.7 |
|  | 50 | 100 |
| 5-methylsulfinyl-1,3,4-thiadiazole-2-carboxylic acid-allylamide | 10 | 99.2 |
|  | 20 | 100 |
|  | 50 | 100 |
| 5-sec.-butylsulfonyl-1,3,4-thiadiazole-2-carbonitrile | 10 | 75 |
|  | 20 | 91 |
|  | 50 | 98 |
| 5-propylsulfonyl-1,3,4-thiadiazole-2-carboxylic acid-isopropylamide | 10 | 98 |
|  | 20 | 99.8 |
|  | 50 | 100 |
| 5-propylsulfonyl-1,3,4-thiadiazole-2-carboxylic acid-butylamide | 10 | 99.2 |
|  | 20 | 99.7 |
|  | 50 | 100 |
| 5-methylsulfonyl-1,3,4-thiadiazole-2-carboyxlic acid-allylamide | 10 | — |
|  | 20 | 100 |
|  | 50 | 100 |
| 5-propylsulfinyl-1,3,4-thiadiazole-2-carboxylic acid-propylamide | 10 | — |
|  | 20 | 99.3 |
|  | 50 | 100 |
| 5-propylsulfinyl-1,3,4-thiadiazole-2-carboxylic acid-allylamide | 10 | — |
|  | 20 | 100 |
|  | 50 | 100 |
| 5-propylsulfinyl-1,3,4-thiadiazole-2-carboxylic acid-isopropylamide | 10 | — |
|  | 20 | 100 |
|  | 50 | 100 |
| 5-methylsulfonyl-1,3,4-thiadiazole-2-carboxylic acid-(2-methoxyethyl)-amide | 10 | — |
|  | 20 | 93 |
|  | 50 | 100 |
| 5-methylsulfinyl-1,3,4-thiadiazole-2-carboxylic acid-ethylamide | 10 | — |
|  | 20 | 100 |
|  | 50 | 100 |
| 5-methylsulfinyl-1,3,4-thiadiazole-2-carboxylic acid-isopropylamide | 10 | — |
|  | 20 | 100 |
|  | 50 | 100 |
| 5-methylsulfonyl-1,3,4-thiadiazole-2-carboxylic acid-cyclopropylamide | 10 | — |
|  | 20 | 98 |
|  | 50 | 100 |
| 5-methylsulfinyl-1,3,4-thiadiazole-2-carboxylic acid-cyclopropylamide | 10 | — |
|  | 20 | 98 |
|  | 50 | 100 |
| 5-methylsulfonyl-1,3,4-thiadiazole-2-carboxylic acid-N,N-trimethyleneamide | 10 | — |
|  | 20 | 99 |
|  | 50 | 100 |
| 5-methylsulfinyl-1,3,4-thiadiazole-2-carboxylic acid-N,N-trimethyleneamide | 10 | — |
|  | 20 | 96 |
|  | 50 | 100 |
| 5-propylsulfonyl-1,3,4-thiadiazole-2-carboxylic acid-dimethylamide | 10 | — |
|  | 20 | 100 |
|  | 50 | 100 |
| 5-butylsulfinyl-1,3,4-thiadiazole-2-carboxamide | 10 | — |
|  | 20 | 95 |
|  | 50 | 100 |
| 5-butylsulfonyl-1,3,4-thiadiazole-2-carbonitrile | 10 | — |
|  | 20 | 95 |
|  | 50 | 100 |
| 5-isobutylsulfonyl-1,3,4-thiadiazole-2-carbonitrile | 10 | — |
|  | 20 | 93 |
|  | 50 | 100 |
| 5-propylsulfonyl-1,3,4-thiadiazole-2-carboxylic acid-hexylamide | 10 | — |
|  | 20 | 100 |
|  | 50 | 100 |

| | Amount of active agent in grams per 100 kg | % activity |
|---|---|---|
| 5-isopropylsulfonyl-1,3,4-thiadiazole-2-carboxylic acid-cyclohexylmethylamide | 10 | — |
| | 20 | 92 |
| | 50 | 97 |
| 5-isopropylsulfinyl-1,3,4-thiadiazole-2-carboxylic acid-cyclohexylmethylamide | 10 | — |
| | 20 | 99 |
| | 50 | 100 |
| 5-propylsulfinyl-1,3,4-thiadiazole-2-carboxylic acid-butylamide | 10 | — |
| | 20 | 100 |
| | 50 | 100 |
| 5-propylsulfinyl-1,3,4-thiadiazole-2-carboxylic acid-sec.-butylamide | 10 | — |
| | 20 | 100 |
| | 50 | 100 |
| 5-propylsulfinyl-1,3,4-thiadiazole-2-carboxylic acid-hexylamide | 10 | — |
| | 20 | 100 |
| | 50 | 100 |
| 5-propylsulfinyl-1,3,4-thiadiazole-2-carboxylic acid-dimethylamide | 10 | — |
| | 20 | 100 |
| | 50 | 100 |
| 5-methylsulfinyl-1,3,4-thiadiazole-2-carbonitrile | 10 | — |
| | 20 | 100 |
| | 50 | 100 |
| 5-methylsulfinyl-1,3,4-thiadiazole-2-carboxamide | 10 | — |
| | 20 | 98 |
| | 50 | 100 |
| 5-isopropylsulfinyl-1,3,4-thiadiazole-2-carboxamide | 10 | — |
| | 20 | — |
| | 50 | 100 |
| 5-isopropylsulfinyl-1,3,4-thiadiazole-2-carbonitrole | 10 | — |
| | 20 | 87 |
| | 50 | 100 |
| 5-pentylsulfonyl-1,3,4-thiadiazole-2-carbonitrile | 10 | — |
| | 20 | — |
| | 50 | 90 |
| 5-hexylsulfonyl-1,3,4-thiadiazole-2-carbonitrile | 10 | — |
| | 20 | — |
| | 50 | 90 |
| 5-pentylsulfonyl-1,3,4-thiadiazole-2-carboxamide | 10 | — |
| | 20 | — |
| | 50 | 80 |
| 5-hexylsulfonyl-1,3,4-thiadiazole-2-carboxamide | 10 | — |
| | 20 | — |
| | 50 | 98 |
| 5-propylsulfonyl-1,3,4-thiadiazole-2-carboxylic acid-N,N-trimethyleneamide | 10 | — |
| | 20 | — |
| | 50 | 100 |
| 5-n-butylsulfonyl-1,3,4-thiadiazole-2-carboxylic acid-N,N-trimethyleneamide | 10 | — |
| | 20 | — |
| | 50 | 100 |
| 5-butylsulfinyl-1,3,4-thiadiazole-2-carbonitrile | 10 | — |
| | 20 | — |
| | 50 | 100 |
| Comparison compound | | |
| methoxyethyl-Hg—silicate | 1.3 | 90 |
| | 2.6 | 100 |

EXAMPLE 20

Spray treatment of rice seedlings infested with *Piricularia oryzae*

Young rice plants were sprayed so as to be dripping wet with the active agent concentrations shown in the sub -continued

| | Concentration of active agent (percentages) | % activity |
|---|---|---|
| diazole-2-carboxylic acid-ethylamide | 0.1 | 90 |
| 5-methylsulfinyl-1,3,4-thiadiazole-2-carboxylic acid-isopropylamide | 0.1 | 90 |
| 5-propylsulfonyl-1,3,4-thiadiazole-2-carboxylic acid-dimethylamide | 0.1 | 93 |
| 5-butylsulfinyl-1,3,4-thiadiazole-2-carboxamide | 0.1 | 93 |
| 5-isobutylsulfonyl-1,3,4-thiadiazole-2-carbonitrile | 0.1 | 100 |
| 5-propylsulfonyl-1,3,4-thiadiazole-2-carboxylic acid-hexylamide | 0.1 | 95 |
| 5-isopropylsulfonyl-1,3,4-thiadiazole-2-carboxylic acid-cyclohexylmethylamide | 0.1 | 98 |
| Comparison compound | | |
| "Blasticidin-S" (antibiotic from Streptomyces griseochromogenes) | 0.02 | 90 |
| | 0.1 | 97 |

EXAMPLE 21

Seed treatment in open field tests regarding infestation by *Tilletia caries*

1 kg of oat seeds each was contaminated with 5 g of spores of the cause of the stinking smuts disease, *Tilletia caries*. Part of the seeds was then treated with the active agents listed below in the table and another part was untreated. All the seeds were then planted in open fields.

The active agents were employed in the form of pulverulent compositions. After about 9 months in case of winter oats and after about 4 months in case of summer oats the diseased heads were counted and on that basis the activity was calculated by the following formula:

$$100 - \frac{100 \cdot \text{infestation of treated heads}}{\text{infestation of untreated heads}} = \% \text{ activity}$$

| Active agent | g active agent/ 100 kg | % activity |
|---|---|---|
| | winter oats | |
| 5-methylsulfonyl-1,3,4-thiadiazole-2-carboxamide | 25 | 100 |
| | 50 | 100 |
| | 100 | 100 |
| 5-methylsulfonyl-1,3,4-thiadiazole-2-carboxylic acid-cyclohexyl-methylamide | 25 | — |
| | 50 | — |
| | 100 | 100 |
| 5-isopropylsulfonyl-1,3,4-thiadiazole-2-carbonitrile | 25 | — |
| | 50 | — |
| | 100 | 100 |
| Comparison compound | | |
| Methoxyethyl-Hg—silicate | 5.3 | 99 |
| Untreated 7.1% infestation | | |
| | summer oats | |
| 5-ethylsulfinyl-1,3,4-thiadiazole-2-carboxamide | 25 | 100 |
| | 50 | 100 |
| 5-methylsulfonyl-1,3,4-thiadiazole-2-carboxylic acid-methylamide | 25 | — |
| | 50 | 100 |
| 5-isobutylsulfonyl-1,3,4-thiadiazole-2-carboxamide | 25 | — |
| | 50 | 99 |
| Comparison compound | | |
| Methoxyethyl-Hg—silicate | 2.6 | 99 |
| Untreated 34.5% infestation | | |

EXAMPLE 22

Seed treatment in open field tests for infestation by *Helminthosporium gramineum*

Barley seeds which had a natural infestation of *Helminthosporium gramineum* which causes the streak disease were seeded in open fields. Part of the seeds had been treated with the active agents listed in the table below and another part had been left untreated.

The active agents were used in the form of pulverulent compositions. After about 8 months in case of winter barley and after about 3 months in case of summer barley the infested plants were counted and the activity was calculated by the formula $$100 - \frac{100 \cdot \text{infestation of treated seeds}}{\text{infestation of untreated seeds}} = \% \text{ activity}$$

| Active agent | g active agent/ 100 kg barley | % activity |
|---|---|---|
| | Winter barley | |
| 5-methylsulfonyl-1,3,4-thiadiazole-2-carboxamide | 25 | 90 |
| | 50 | 96 |
| | 75 | 100 |
| | 100 | 100 |
| 5-isopropylsulfonyl-1,3,4-thiadiazole-2-carbonitrile | 25 | — |
| | 50 | — |
| | 75 | 99 |
| | 100 | 100 |
| 5-methylsulfonyl-1,3,4-thiadiazole-2-carboxylic acid-methylamide | 25 | 99.5 |
| | 50 | 99.5 |
| | 75 | 100 |
| 5-methylsulfonyl-1,3,4-thiadiazole-2-carboxylic acid-dimethylamide | 25 | — |
| | 50 | 98 |
| | 75 | — |
| | 100 | 100 |
| 5-isobutylsulfonyl-1,3,4-thiadiazole-2-carboxamide | 25 | — |
| | 50 | 100 |
| | 75 | 100 |
| | 100 | 100 |
| 5-ethylsulfonyl-1,3,4-thiadiazole-2-carboxylic acid-methylamide | 25 | — |
| | 50 | 100 |
| | 75 | — |
| | 100 | 100 |
| 5-ethylsulfonyl-1,3,4-thiadiazole-2-carboxylic acid-dimethylamide | 25 | — |
| | 50 | 99.5 |
| | 75 | — |
| | 100 | 100 |
| Comparison compound | | |
| Methoxyethyl-Hg—silicate | 5.2 | 100 |
| | 2.6 | 99.4 |
| Untreated 11.2% infestation | | |
| | Summer barley | |
| 5-methylsulfonyl-1,3,4-thiadiazole-2-carboxamide | 25 | 95 |
| | 50 | 100 |
| | 100 | 100 |
| 5-isopropylsulfonyl-1,3,4-thiadiazole-2-carbonitrile | 25 | 100 |
| | 50 | 99.8 |
| | 100 | 100 |
| 5-methylsulfonyl-1,3,4-thiadiazole-2-carboxylic acid-methylamide | 25 | 93 |
| | 50 | 100 |
| | 100 | 100 |
| 5-isobutylsulfonyl-1,3,4-thiadiazole-2-carboxamide | 25 | — |
| | 50 | 99.5 |
| | 100 | 100 |
| 5-ethylsulfonyl-1,3,4-thiadiazole-2-carboxylic acid-methylamide | 25 | — |
| | 50 | 100 |
| | 100 | 100 |
| 5-ethylsulfonyl-1,3,4-thiadiazole-2-carboxylic acid-dimethylamide | 25 | — |
| | 50 | 99.5 |
| | 100 | 100 |
| 5-ethylsulfonyl-1,3,4-thiadiazole-2-carboxylic acid-butylamide | 25 | — |
| | 50 | — |
| | 100 | 100 |
| 5-ethylsulfonyl-1,3,4-thiadiazole-2-carboxylic acid- | 25 | — |
| | 50 | — |

-continued

| | g active agent/ 100 kg barley | % activity |
|---|---|---|
| cyclopropylamide | 200 | 100 |
| 5-ethylsulfonyl-1,3,4-thiadiazole-2-carboxylic acid-ethylamide | 25 | 98 |
| | 50 | 99.5 |
| | 100 | 100 |
| 5-ethylsulfonyl-1,3,4-thiadiazole-2-carboxylic acid-propylamide | 25 | 95 |
| | 50 | 99.3 |
| | 100 | 100 |
| 5-ethylsulfonyl-1,3,4-thiadiazole-2-carboxylic acid-(N-butyl-N-methyl)-amide | 25 | 94 |
| | 50 | 96.9 |
| | 100 | 99.5 |
| 5-ethylsulfonyl-1,3,4-thiadiazole-2-carboxylic acid-(2-methoxyethyl)-amide | 25 | 92 |
| | 50 | 98 |
| | 100 | 99.8 |
| 5-ethylsulfonyl-1,3,4-thiadiazole-2-carboxylic acid-(3-methoxypropyl)-amide | 25 | 94 |
| | 50 | 96 |
| | 100 | 100 |
| 5-ethylsulfonyl-1,3,4-thiadiazole-2-carboxylic acid-isopropyl-amide | 25 | 96 |
| | 50 | 100 |
| | 100 | 99.8 |
| 5-ethylsulfonyl-1,3,4-thiadiazole-2-carboxylic acid-allylamide | 25 | 97 |
| | 50 | 100 |
| | 100 | 100 |
| 5-ethylsulfonyl-1,3,4-thiadiazole-2-carboxylic acid-N,N-tetramethyleneamide | 25 | — |
| | 50 | 100 |
| | 100 | — |
| 5-ethylsulfonyl-1,3,4-thiadiazole-2-carboxylic acid-(N,N-3-oxapentamethyleneamide) | 25 | — |
| | 50 | 99.3 |
| | 100 | — |
| 5-propylsulfinyl-1,3,4-diazole-2-carbonitrile | 25 | — |
| | 50 | 99.3 |
| | 100 | — |
| 5-ethylsulfinyl-1,3,4-thiadiazole-2-carbonitrile | 25 | — |
| | 50 | 100 |
| | 100 | — |
| 5-methylsulfonyl-1,3,4-thiadiazole-2-carboxylic acid-ethylamide | 25 | — |
| | 50 | 100 |
| | 100 | — |
| 5-methylsulfonyl-1,3,4-thiadiazole-2-carboxylic acid-isopropylamide | 25 | — |
| | 50 | 100 |
| | 100 | — |
| 5-methylsulfonyl-1,3,4-thiadiazole-2-carboxylic acid-propylamide | 25 | — |
| | 50 | 100 |
| | 100 | — |
| 5-methylsulfonyl-1,3,4-thiadiazole-2-carboxylic acid-butylamide | 25 | — |
| | 50 | 99.3 |
| | 100 | — |
| 5-methylsulfinyl-1,3,4-thiadiazole-2-carboxylic acid-propylamide | 25 | — |
| | 50 | 97 |
| | 100 | — |
| 5-methylsulfinyl-1,3,4-thiadiazole-2-carboxylic acid-butylamide | 25 | — |
| | 50 | 100 |
| | 100 | — |
| 5-sec.-butylsulfonyl-1,3,4-thiadiazole-2-carboxyamide | 25 | — |
| | 50 | 94 |
| | 100 | — |
| 5-methylsulfinyl-1,3,4-thiadiazole-2-carboxylic acid-allylamide | 25 | — |
| | 50 | 100 |
| | 100 | — |
| Comparison compound | | |
| Methoxyethyl-Hg—silicate | 10.4 | 100 |
| | 5.2 | 99.8 |
| Untreated 23.9% infestation | | |

EXAMPLE 23
Oat seed treatment for *Ustilago avenae*

Oat seeds were dipped into a suspension of the spores of *Ustilago avenae* which causes the oat smuts fungus. The seeds were then exposed in a vacuum desiccator several times to a change from atmospheric to subatmospheric pressure. After drying the seeds were treated with the active agents listed in the subsequent table. The agents were used in the form of pulverulent compositions. 10 weeks after seeding the diseased panicles were counted and on this basis the activity was calculated by the formula.

$$100 - \frac{100 \cdot \text{infestation (untreated)}}{\text{infestation (untreated)}} = \% \text{ activity}$$

| Active agent | g active agent/ 100 kg | % activity |
|---|---|---|
| 5-methylsulfonyl-1,3,4-thiadiazole-2-carboxamide | 100 | 84 |
| | 150 | 90 |
| 5-isopropylsulfonyl-1,3,4-thiadiazole-2-carbonitrile | 100 | 97 |
| | 150 | — |
| 5-methylsulfonyl-1,3,4-thiadiazole-2-carboxylic acid-methylamide | 100 | 90 |
| | 150 | — |
| 5-isobutylsulfonyl-1,3,4-thiadiazole-2-carboxamide | 100 | 87 |
| | 150 | — |
| Comparison compound | | |
| Methoxyethyl-Hg—silicate | 16 | 66 |
| Untreated 16.6% infestation | | |

EXAMPLE 24
Effects of prophylactic leaf treatment of grapevines in the hothouse against *Plasmopara viticola*

Young grapevine plants having from 5 to 8 leaves were sprayed dripping wet with the concentrations of active agents stated in the table below. After drying of the spray deposit the leaves were sprayed with an aqueous suspension of sporangia of the fungus (about 20,000 per ml); the spraying was applied to the bottom side of the leaves. The plants were then immediately incubated in a hothouse at a temperature of 22° to 24° C. and at maximum water saturation in the atmosphere. Beginning with the second day the humidity of the air was reduced for 3 to 4 days to normal level (30 to 70% saturation) and was then maintained for another day on the level of full saturation. Subsequently, the percentage portion of the fungus infested surface of each leaf was noted and the average per treatment was calculated in order to determine the fungicidal activity. This was done on the basis of the following formula:

$$100 - \frac{100 \cdot \text{infestation (untreated)}}{\text{infestation (untreated)}} = \% \text{ activity}$$

The active compounds were applied in the form of a 20% concentration spray powder.

| Active agent | Concentration of active agent | % activity |
|---|---|---|
| 5-methylsulfonyl-1,3,4-thiadiazole-2-carboxylic acid hexahydrobenzylamide | 0.001 | 76 |
| | 0.005 | 88 |
| | 0.025 | 97 |
| 5-propylsulfonyl-1,3,4-thiadiazole-2-carboxamide | 0.001 | — |
| | 0.005 | 89 |
| | 0.025 | 95 |
| 5-ethylsulfonyl-1,3,4-thiadiazole-2-carboxylic acid-ethylamide | 0.001 | — |
| | 0.005 | — |
| | 0.025 | 98 |
| 5-ethylsulfonyl-1,3,4-thiadiazole-2-carboxylic acid-(N-butyl-N-methyl)-amide | 0.001 | 100 |
| | 0.005 | 100 |
| | 0.025 | 100 |
| 5-ethylsulfonyl-1,3,4-thiadiazole-2-carboxylic acid-(3-methoxypropyl)-amide | 0.001 | — |
| | 0.005 | — |
| | 0.025 | 90 |
| 5-ethylsulfonyl-1,3,4-thiadiazole-2-carboxylic acid-isopropyl-amide | 0.001 | — |
| | 0.005 | — |
| | 0.025 | 92 |

| Active agent | Concentration of active agent | % activity |
|---|---|---|
| 5-ethylsulfonyl-1,3,4-thiadiazole-2-carboxylic acid-allylamide | 0.001 | 98 |
| | 0.005 | 96 |
| | 0.025 | 99.4 |
| 5-ethylsulfonyl-1,3,4-thiadiazole-2-carboxylic acid-octylamide | 0.001 | — |
| | 0.005 | — |
| | 0.025 | 90 |
| 5-ethylsulfonyl-1,3,4-thiadiazole-2-carboxylic acid-N,N-tetramethyleneamide | 0.001 | 91 |
| | 0.005 | 99 |
| | 0.025 | 100 |
| 5-propylsulfinyl-1,3,4-thiadiazole-2-carbonitrile | 0.001 | 100 |
| | 0.005 | 100 |
| | 0.025 | 100 |
| 5-ethylsulfinyl-1,3,4-thiadiazole-2-carbonitrile | 0.001 | 89 |
| | 0.005 | 96 |
| | 0.025 | 100 |
| 5-methylsulfonyl-1,3,4-thiadiazole-2-carboxylic acid-ethylamide | 0.001 | — |
| | 0.005 | 81 |
| | 0.025 | 97 |
| 5-methylsulfonyl-1,3,4-thiadiazole-2-carboxylic acid-isopropylamide | 0.001 | — |
| | 0.005 | 76 |
| | 0.025 | 96 |
| 5-methylsulfonyl-1,3,4-thiadiazole-2-carboxylic acid-propylamide | 0.001 | — |
| | 0.005 | 82 |
| | 0.025 | 95 |
| 5-methylsulfonyl-1,3,4-thiadiazole-2-carboxylic acid-butylamide | 0.001 | 83 |
| | 0.005 | 99.1 |
| | 0.025 | 99.2 |
| 5-methylsulfinyl-1,3,4-thiadiazole-2-carboxylic acid-propylamide | 0.001 | — |
| | 0.005 | 75 |
| | 0.025 | 99 |
| 5-methylsulfinyl-1,3,4-thiadiazole-2-carboxylic acid-butylamide | 0.001 | — |
| | 0.005 | — |
| | 0.025 | 93 |
| 5-propylsulfonyl-1,3,4-thiadiazole-2-carboxylic acid-propylamide | 0.001 | — |
| | 0.005 | — |
| | 0.025 | 93 |
| 5-methylsulfinyl-1,3,4-thiadiazole-2-carboxylic acid-allylamide | 0.001 | — |
| | 0.005 | — |
| | 0.025 | 90 |
| 5-methylsulfinyl-1,3,4-thiadiazole-2-carboxylic acid-(2-methoxyethyl)-amide | 0.001 | — |
| | 0.005 | — |
| | 0.025 | 96 |
| 5-methylsulfinyl-1,3,4-thiadiazole-2-carboxylic acid-ethylamide | 0.001 | — |
| | 0.005 | — |
| | 0.025 | 96 |
| 5-methylsulfinyl-1,3,4-thiadiazole-2-carboxylic acid-isopropylamide | 0.001 | — |
| | 0.005 | — |
| | 0.025 | 90 |
| 5-methylsulfinyl-1,3,4-thiadiazole-2-carboxylic acid-cyclopropylamide | 0.001 | — |
| | 0.005 | 80 |
| | 0.025 | 90 |
| 5-methylsulfonyl-1,3,4-thiadiazole-2-carboxylic acid-N,N-trimethyleneamide | 0.001 | — |
| | 0.005 | 84 |
| | 0.025 | 90 |
| 5-methylsulfinyl-1,3,4-thiadiazole-2-carboxylic acid-N,N-trimethyleneamide | 0.001 | 86 |
| | 0.005 | 93 |
| | 0.025 | 94 |
| 5-propylsulfonyl-1,3,4-thiadiazole-2-carboxylic acid-dimethylamide | 0.001 | — |
| | 0.005 | 75 |
| | 0.025 | 90 |
| 5-butylsulfonyl-,3,4-thiadiazole-2-carboxaimide | 0.001 | — |
| | 0.005 | 73 |
| | 0.025 | 90 |
| 5-butylsulfinyl-1,3,4-thiadiazole-2-carboxamide | 0.001 | 75 |
| | 0.005 | 99.8 |
| | 0.025 | 100 |
| 5-butylsulfonyl-1,3,4-thiadiazole-2-carbonitrile | 0.001 | — |
| | 0.005 | 91 |
| | 0.025 | 93 |
| 5-isobutylsulfonyl-1,3,4-thiadiazole-2-carbonitrile | 0.001 | 79 |
| | 0.005 | 87 |
| | 0.025 | 99 |
| 5-propylsulfonyl-1,3,4-thiadiazole-2-carboxylic acid-hexylamide | 0.001 | 88 |
| | 0.005 | 98 |
| | 0.025 | 100 |
| 5-isopropylsulfonyl-1,3,4-thiadiazole-2-carboxylic acid-cyclohexylmethylamide | 0.001 | — |
| | 0.005 | 92 |
| | 0.025 | 97 |
| 5-propylsulfinyl-1,3,4-thiadiazole-2-carboxylic acid-butylamide | 0.001 | — |
| | 0.005 | 91 |
| | 0.025 | 99.1 |
| 5-propylsulfinyl-1,3,4-thiadiazole-2-carboxylic acid-sec.-butylamide | 0.001 | 86 |
| | 0.005 | 92 |
| | 0.025 | 92 |
| 5-propylsulfinyl-1,3,4-thiadiazole-2-carboxylic acid-hexylamide | 0.001 | 95 |
| | 0.005 | 99.1 |
| | 0.025 | 100 |
| 5-pentylsulfonyl-1,3,4-thiadiazole-2-carbonitrile | 0.001 | — |
| | 0.005 | — |
| | 0.025 | 90 |
| 5-hexylsulfonyl-1,3,4-thiadiazole-2-carbonitrile | 0.001 | — |
| | 0.005 | — |
| | 0.025 | 90 |
| 5-hexylsulfonyl-1,3,4-thiadiazole-2-carboxamide | 0.001 | — |
| | 0.005 | — |
| | 0.025 | 90 |

EXAMPLE 25

Effects of a prophylactic leaf treatment of tomato plants against *Botrytis cinerea*

Young tomato plants were sprayed dripping wet with the concentrations of the active agents as indicated in the subsequent table. After drying of the spray deposit the treated plants and also untreated control plants were inoculated by spraying with a suspension of spores (about 1 million per ml of fruit juice solution) of *Botrytis cinerea* and were incubated in moist condition in a hothouse at about 20° C. After the collapse of the untreated plants (indicating 100% infestation) the degree of infestation of the treated plants was determined and the fungicidal activity was calculated on the basis of the following formula $$100 - \frac{100 \cdot \text{infestation (untreated)}}{\text{infestation (untreated)}} = \% \text{ activity}$$

The active agents were applied in the form of 20% concentration spray powders.

| Active agent | % activity at a concentration of 0.025 of the active agent |
|---|---|
| 5-methylsulfonyl-1,3,4-thiadiazole-2-carboxylic acid-methylamide | 78 |
| 5-propylsulfonyl-1,3,4-thiadiazole-2-carboxyamide | 94 |
| 5-propylsulfonyl-1,3,4-thiadiazole-2-carboxylic acid-methylamide | 88 |
| 5-ethylsulfonyl-1,3,4-thiadiazole-2-carboxylic acid-octylamide | 87 |
| 5-ethylsulfonyl-1,3,4-thiadiazole-2-carboxylic acid-N,N-tetramethyleneamide | 75 |
| 5-ethylsulfonyl-1,3,4-thiadiazole-2-carboxylic acid-cyclooctylamide | 93 |
| 5-methylsulfonyl-1,3,4-thiadiazole-2-carboxylic acid-propylamide | 76 |
| 5-methylsulfonyl-1,3,4-thiadiazole-2-carboxylic acid-butylamide | 76 |
| 5-propylsulfonyl-1,3,4-thiadiazole-2-carboxylic acid-propylamide | 80 |
| 5-methylsulfinyl-1,3,4-thiadiazole-2-carboxylic acid-ethylamide | 75 |
| 5-methysulfonyl-1,3,4-thiadiazole-2-carboxylic acid-cyclopropylamide | 75 |
| 5-propylsulfonyl-1,3,4-thiadiazole-2-carboxylic acid-hexylamide | 78 |
| 5-propylsulfinyl-1,3,4-thiadiazole-2-carboxylic acid-butylamide | 80 |
| 5-propylsulfinyl-1,3,4-thiadiazole-2-carboxylic acid-sec.-butylamide | 80 |

-continued

| Active agent | % activity at a concentration of 0.025 of the active agent |
|---|---|
| 5-propylsulfinyl-1,3,4-thiadiazole-2-carboxylic acid-hexylamide | 80 |
| 5-propylsulfinyl-1,3,4-thiadiazole-2-carboxylic acid-dimethylamide | 80 |
| 5-pentylsulfonyl-1,3,4-thiadiazole-2-carbonitrile | 86 |
| 5-hexylsulfonyl-1,3,4-thiadiazole-2-carbonitrile | 86 |
| 5-pentylsulfonyl-1,3,4-thiadiazole-2-carboxamide | 87 |
| 5-hexylsulfonyl-1,3,4-thiadiazole-2-carboxamide | 87 |
| 5-propylsulfonyl-1,3,4-thiadiazole-2-carboxylic acid-N,N-trimethylene-amide | 87 |

EXAMPLE 26

Treatment of rye seeds against *Fusarium nivale*

Rye seeds with a natural infestation by *Fusarium nivale* were seeded in earth filled pots and left for germination at about 6° C. Part of the seeds was treated before seeding with the active agents as appears from the subsequent table and part was untreated. After emergence of the seedlings the plants were illuminated with artificial light for 12 hours each day. After about 4 weeks the degree of infestation was determined in percentages. The fungicidal activity was calculated on the basis of the following formula:

$$100 - \frac{100 \cdot \text{infestation (untreated)}}{\text{infestation (untreated)}} = \% \text{ activity}$$

The active agents were used in the form of 20% concentration compositions.

| Active agent | % activity; amount of active agent: 100 g/100 kg |
|---|---|
| 5-methylsulfonyl-1,3,4-thiadiazole-2-carboxamide | 99 |
| 5-ethylsulfonyl-1,3,4-thiadiazole-2-carboxamide | 99.2 |
| 5-ethylsulfonyl-1,3,4-thiadiazole-2-carbonitrile | 92 |
| 5-ethylsulfinyl-1,3,4-thiadiazole-2-carboxamide | 93 |
| 5-methylsulfonyl-1,3,4-thiadiazole-2-carboxylic acid-methylamide | 100 |
| 5-isobutylsulfonyl-1,3,4-thiadiazole-2-carboxamide | 99.2 |
| 5-ethylsulfonyl-1,3,4-thiadiazole-2-carboxylic acid-methylamide | 100 |
| 5-ethylsulfonyl-1,3,4-thiadiazole-2-carboxylic acid-dimethylamide | 100 |
| 5-ethylsulfonyl-1,3,4-thiadiazole-2-carboxylic acid-allylamide | 94 |

EXAMPLE 27

Effects of the treatment of oat seeds against *Septoria nodorum*

Oat seeds with a natural infestation by *Septoria nodorum* were treated with the active agents as indicated in the table below. They were then seeded on a moist substrate for germination. As a control untreated seeds were likewise seeded. At about 6° C. the seed was incubated in an air-conditioned chamber until after 4 weeks the proportion of diseased seeds could be determined and the activity of the fungicidal compounds was calculated on the basis of the following formula:

$$100 - \frac{100 \cdot \text{fraction of diseased seeds treated}}{\text{fraction of diseased seeds untreated}} = \% \text{ activity}$$

The active agents were applied in the form of 20% concentration pulverulent compositions.

| Active agent | % activity in case of 50 g active agent/ 100 kg seeds |
|---|---|
| 5-methylsulfonyl-1,3,4-thiadiazole-2-carboxamide | 91 |
| 5-methylsulfonyl-1,3,4-thiadiazole-2-carboxylic acid methylamide | 93 |
| 5-ethylsulfonyl-1,3,4-thiadiazole-2-carboxylic acid methylamide | 72 |
| 5-ethylsulfonyl-1,3,4-thiadiazole-2-carboxylic acid dimethylamide | 86 |
| 5-ethylsulfonyl-1,3,4-thiadiazole-2-carboxylic acid propylamide | 81 |
| 5-ethylsulfonyl-1,3,4-thiadiazole-2-carboxylic acid (2-methoxyethyl)-amide | 86 |
| 5-ethylsulfonyl-1,3,4-thiadiazole-2-carboxylic acid (3-methoxypropyl)-amide | 86 |
| 5-ethylsulfonyl-1,3,4-thiadiazole-2-carboxylic acid isopropylamide | 86 |
| 5-ethylsulfonyl-1,3,4-thiadiazole-2-carboxylic acid allylamide | 72 |
| Comparison compound | 1.3 g active agent/100 kg seeds |
| Methoxyethyl-Hg-silicate | 86 |
| Untreated | 75% infested |

EXAMPLE 28

Prophylactic leaf treatment of apples in open field test against *Venturia inaequalis*

Apple shoots with young leaves were treated with the agents stated in the subsequent table until they were dripping wet. After drying of the spray deposits these shoots and also untreated shoots were inoculated by uniform spraying with a suspension of conidia spores of *Venturia inaequalis* in a 3% aqueous glucose solution (400,000 spores/ml).

Subsequently, each apple shoot was covered with a polyethylene bag so as to obtain favorable conditions for the infection. After more than 48 hours the bags were removed. The scab infestation of the leaves was determined after 3 weeks by estimating the degree of scab coverage in percentage of each leaf surface. The activity of the fungicidal agent was calculated on this basis by the following formula:

$$100 - \frac{100 \cdot \text{scab infestation, treated}}{\text{scab infestation, untreated}} = \% \text{ activity}$$

The active agents were employed as a 50% concentration spray powder.

| Active agent | Concentration of active agent in gram | % activity |
|---|---|---|
| 5-isopropylsulfonyl-1,3,4-thiadiazole-2-carbonitrole | 0.005 | 97 |
|  | 0.025 | 100 |
| 5-methylsulfonyl-1,3,4-thiadiazole-2-carboxylic acid methylamide | 0.005 | 90 |
|  | 0.025 | 92 |
| 5-isobutylsulfonyl-1,3,4-thiadiazole-2-carboxamide | 0.005 | 87 |
|  | 0.025 | 95 |
| 5-methylsulfonyl-1,3,4-thiadiazole-2-carboxylic acid ethylamide | 0.005 | 81 |
|  | 0.025 | 97 |
| 5-methylsulfonyl-1,3,4-thiadiazole-2-carboxylic acid isopropylamide | 0.005 | 85 |
|  | 0.025 | 100 |
| 5-methylsulfonyl-1,3,4-thiadiazole-2-carboxylic acid propylamide | 0.005 | 98 |
|  | 0.025 | 99.7 |
| 5-methylsulfonyl-1,3,4-thiadiazole-2-carboxylic acid butylamide | 0.005 | 94 |
|  | 0.025 | 99 |
| 5-methylsulfinyl-1,3,4-thiadiazole-2-carboxylic acid propylamide | 0.005 | 62 |
|  | 0.025 | 99.7 |
| 5-methylsulfinyl-1,3,4-thiadiazole-2-carboxylic acid butylamide | 0.005 | 86 |
|  | 0.025 | 99 |
| 5-methylsulfinyl-1,3,4-thiadiazole-2-carboxylic acid isopropylamide | 0.005 | 71 |
|  | 0.025 | 90 |
| Comparison compound |  |  |
| 2,3-dinitrilo-1,4-anthraquinone | 0.005 | 86 |
|  | 0.025 | 94 |
| Untreated | 96% infestation |  |

EXAMPLE 29

Treatment of wheat and barley seeds in open field tests against *Ustilago nuda*

Winter wheat seeds which had been infested with the smut cause *Ustilago nuda tritici* and winter barley seeds infested with *Ustilago nuda nuda* were treated with the agents listed in the table below and were seeded at seeding time in open fields. As a control untreated seeds were likewise included in the seed. After eight months the affected heads were counted for each test group and their proportion was calculated in order to find the fungicidal activity by the following formula:

$$100 - \frac{100 \cdot \text{fraction of diseased heads treated}}{\text{fraction of diseased heads untreated}} = \% \text{ activity}$$

The active compounds were employed in the form of 20% concentration powder compositions.

| Active agent | amount of active agent in gram/100 kg seeds | % activity winter oats | % activity winter barley |
|---|---|---|---|
| 5-isopropylsulfonyl-1,3,4-thiadiazole-2-carbonitrile | 100 | 70 | 93 |
| 5-isobutylsulfonyl-1,3,4-thiadiazole-2-carboxamide | 100 | 75 | 79 |
| Untreated |  | 4.33% | 1.34% |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. 1,3,4-thiadiazole-2-carboxylic acid derivatives of the formula

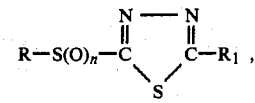

wherein R is $C_1-C_6$-alkyl, $C_2-C_6$-alkenyl, $C_2-C_6$-alkinyl or $C_3-C_6$-cycloalkyl, $R_1$ is $C_1-C_6$-alkoxycarbonyl, aminocarbonyl, $C_1-C_8$-alkylaminocarbonyl, $C_3-C_6$-cycloalkylaminocarbonyl, di-$C_1-C_8$-alkylaminocarbonyl, cyclohexylmethylaminocarbonyl, methoxy-$C_2-C_3$-alkylaminocarbonyl, morpholinocarbonyl, pyrrolidinocarbonyl, piperidinocarbonyl or cyano, and n is 0,1 or 2.

2. 1,3,4-thiadiazole-2-carboxylic acid derivatives of the formula

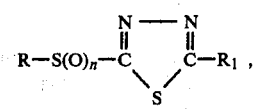

wherein R is $C_1-C_6$-alkyl, $C_2-C_6$-alkenyl, $C_2-C_6$-alkinyl or $C_3-C_6$-cycloalkyl, $R_1$ is allylaminocarbonyl, N,N-trimethylene aminocarbonyl or cyclooctylaminocarbonyl and n is 0,1 or 2.

3. The compound as defined in claim 1 which is 5-ethylsulfinyl-1,3,4-thiadiazole-2-carboxamide.

4. The compound as defined in claim 1 which is 5-methylsulfonyl-1,3,4-thiadiazole-2-carboxamide.

5. The compound as defined in claim 1 which is 5-isopropylsulfonyl-1,3,4-thiadiazole-2-carboxamide.

6. The compound as defined in claim 1 which is 5-methylsulfonyl-1,3,4-thiadiazole-2-carbonitrile.

7. The compound as defined in claim 1 which is 5-methylsulfonyl-1,3,4-thiadiazole-2-carboxylic acid ethylester.

8. The compound as defined in claim 1 which is 5-methylsulfonyl-1,3,4-thiadiazole-2-carboxylic acid cyclohexylmethylamide.

9. The compound as defined in claim 1 which is 5-ethylsulfonyl-1,3,4-thiadiazole-2-carboxamide.

10. The compound as defined in claim 1 which is 5-ethylsulfonyl-1,3,4-thiadiazole-2-carbonitrile.

11. The compound as defined in claim 1 which is 5-isopropylsulfonyl-1,3,4-thiadiazole-2-carbonitrile.

12. The compound as defined in claim 1 which is 5-methylsulfonyl-1,3,4-thiadiazole-2-carboxylic acid methylamide.

13. The compound as defined in claim 1 which is 5-methylsulfonyl-1,3,4-thiadiazole-2-carboxylic acid dimethylamide.

14. The compound as defined in claim 1 which is 5-isobutylsulfonyl-1,3,4-thiadiazole-2-carboxamide.

15. The compound as defined in claim 1 which is 5-ethylsulfonyl-1,3,4-thiadiazole-2-carboxylic acid methylamide.

16. The compound as defined in claim 1 which is 5-ethylsulfonyl-1,3,4-thiadiazole-2-carboxylic acid dimethylamide.

17. The compound as defined in claim 1 which is 5-propylsulfonyl-1,3,4-thiadiazole-2-carboxamide.

18. The compound as defined in claim 1 which is 5-propylsulfonyl-1,3,4-thiadiazole-2-carboxylic acid methylamide.

19. The compound as defined in claim 1 which is 5-ethylsulfonyl-1,3,4-thiadiazole-2-carboxylic acid butylamide.

20. The compound as defined in claim 1 which is 5-ethylsulfonyl-1,3,4-thiadiazole-2-carboxylic acid ethylester.

21. The compound as defined in claim 1 which is 5-ethylsulfonyl-1,3,4-thiadiazole-2-carboxylic acid cyclopropylamide.

22. The compound as defined in claim 1 which is 5-methylsulfonyl-1,3,4-thiadiazole-2-carboxylic acid methylester.

23. The compound as defined in claim 1 which is 5-ethylsulfonyl-1,3,4-thiadiazole-2-carboxylic acid propylamide.

24. The compound as defined in claim 1 which is 5-ethylsulfonyl-1,3,4-thiadiazole-2-carboxylic acid (N-butyl, N-methyl)-amide.

25. The compound as defined in claim 1 which is 5-ethylsulfonyl-1,3,4-thiadiazole-2-carboxylic acid (2-methoxyethyl)-amide.

26. The compound as defined in claim 1 which is 5-ethylsulfonyl-1,3,4-thiadiazole-2-carboxylic acid (3-methoxypropyl)-amide.

27. The compound as defined in claim 1 which is 5-ethylsulfonyl-1,3,4-thiadiazole-2-carboxylic acid isopropylamide.

28. The compound as defined in claim 1 which is 5-methylthio-1,3,4-thiadiazole-2-carbonitrile.

29. The compound as defined in claim 1 which is 5-ethylsulfonyl-1,3,4-thiadiazole-2-carboxylic acid allylamide.

30. The compound as defined in claim 1 which is 5-ethylsulfonyl-1,3,4-thiadiazole-2-carboxylic acid octylamide.

31. The compound as defined in claim 1 which is 5-ethylsulfonyl-1,3,4-thiadiazole-2-carboxylic acid-N,N-tetramethyleneamide.

32. The compound as defined in claim 1 which is 5-ethylsulfonyl-1,3,4-thiadiazole-2-carboxylic acid (N,N-3-oxapentamethyleneamide).

33. The compound as defined in claim 2 which is 5-ethylsulfonyl-1,3,4-thiadiazole-2-carboxylic acid cyclooctylamide.

34. The compound as defined in claim 1 which is 5-propylsulfonyl-1,3,4-thiadiazole-2-carboxylic acid ethylester.

35. The compound as defined in claim 1 which is 5-propylsulfonyl-1,3,4-thiadiazole-2-carbonitrile.

36. The compound as defined in claim 1 which is 5-propylsulfinyl-1,3,4-thiadiazole-2-carbonitrile.

37. The compound as defined in claim 1 which is 5-ethylsulfinyl-1,3,4-thiadiazole-2-carbonitrile.

38. The compound as defined in claim 1 which is 5-methylsulfonyl-1,3,4-thiadiazole-2-carboxylic acid ethylamide.

39. The compound as defined in claim 1 which is 5-methylsulfonyl-1,3,4-thiadiazole-2-carboxylic acid isopropylamide.

40. The compound as defined in claim 1 which is 5-methylsulfonyl-1,3,4-thiadiazole-2-carboxylic acid propylamide.

41. The compound as defined in claim 1 which is 5-methylsulfonyl-1,3,4-thiadiazole-2-carboxylic acid butylamide.

42. The compound as defined in claim 1 which is 5-methylsulfinyl-1,3,4-thiadiazole-2-carboxylic acid propylamide.

43. The compound as defined in claim 1 which is 5-methylsulfinyl-1,3,4-thiadiazole-2-carboxylic acid butylamide.

44. The compound as defined in claim 1 which is 5-propylsulfonyl-1,3,4-thiadiazole-2-carboxylic acid ethylamide.

45. The compound as defined in claim 1 which is 5-propylsulfonyl-1,3,4-thiadiazole-2-carboxylic acid propylamide.

46. The compound as defined in claim 2 which is 5-propylsulfonyl-1,3,4-thiadiazole-2-carboxylic acid allylamide.

47. The compound as defined in claim 1 which is 5-sec.-butylsulfonyl-1,3,4-thiadiazole-2-carboxylic acid ethylester.

48. The compound as defined in claim 1 which is 5-sec.-butylsulfonyl-1,3,4-thiadiazole-2-carboxamide.

49. The compound as defined in claim 2 which is 5-methylsulfinyl-1,3,4-thiadiazole-2-carboxylic acid allylamide.

50. The compound as defined in claim 1 which is 5-sec.-butylsulfinyl-1,3,4-thiadiazole-2-carboxamide.

51. The compound as defined in claim 1 which is 5-sec.-butylsulfonyl-1,3,4-thiadiazole-2-carbonitrile.

52. The compound as defined in claim 1 which is 5-propylsulfonyl-1,3,4-thiadiazole-2-carboxylic acid isopropylamide.

53. The compound as defined in claim 1 which is 5-propylsulfonyl-1,3,4-thiadiazole-2-carboxylic acid butylamide.

54. The compound as defined in claim 2 which is 5-methylsulfonyl-1,3,4-thiadiazole-2-carboxylic acid allylamide.

55. The compound as defined in claim 1 which is 5-propylsulfinyl-1,3,4-thiadiazole-2-carboxylic acid ethylamide.

56. The compound as defined in claim 1 which is 5-propylsulfinyl-1,3,4-thiadiazole-2-carboxylic acid propylamide.

57. The compound as defined in claim 2 which is 5-propylsulfinyl-1,3,4-thiadiazole-2-carboxylic acid allylamide.

58. The compound as defined in claim 1 which is 5-propylsulfinyl-1,3,4-thiadiazole-2-carboxylic acid isopropylamide.

59. The compound as defined in claim 1 which is 5-methylsulfonyl-1,3,4-thiadiazole-2-carboxylic acid (2-methoxyethyl)-amide.

60. The compound as defined in claim 1 which is 5-methylsulfonyl-1,3,4-thiadiazole-2-carboxylic acid (2-methoxyethyl)-amide.

61. The compound as defined in claim 1 which is 5-methylsulfonyl-1,3,4-thiadiazole-2-carboxylic acid (3-methoxypropyl)-amide.

62. The compound as defined in claim 1 which is 5-methylsulfinyl-1,3,4-thiadiazole-2-carboxylic acid (3-methoxypropyl)-amide.

63. The compound as defined in claim 1 which is 5-methylsulfinyl-1,3,4-thiadiazole-2-carboxylic acid ethylamide.

64. The compound as defined in claim 1 which is 5-methylsulfinyl-1,3,4-thiadiazole-2-carboxylic acid isopropylamide.

65. The compound as defined in claim 1 which is 5-methylsulfonyl-1,3,4-thiadiazole-2-carboxylic acid cyclopropylamide.

66. The compound as defined in claim 1 which is 5-methylsulfinyl-1,3,4-thiadiazole-2-carboxylic acid cyclopropylamide.

67. The compound as defined in claim 2 which is 5-methylsulfonyl-1,3,4-thiadiazole-2-carboxylic acid N,N-trimethyleneamide.

68. The compound as defined in claim 2 which is 5-methylsulfinyl-1,3,4-thiadiazole-2-carboxylic acid N,N-trimethyleneamide.

69. The compound as defined in claim 1 which is 5-propylsulfonyl-1,3,4-thiadiazole-2-carboxylic acid sec.-butylamide.

70. The compound as defined in claim 1 which is 5-propylsulfonyl-1,3,4-thiadiazole-2-carboxylic acid dimethylamide.

71. The compound as defined in claim 1 which is 5-butylsulfonyl-1,3,4-thiadiazole-2-carboxamide.

72. The compound as defined in claim 1 which is 5-butylsulfinyl-1,3,4-thiadiazole-2-carboxamide.

73. The compound as defined in claim 1 which is 5-butylsulfonyl-1,3,4-thiadiazole-2-carbonitrile.

74. The compound as defined in claim 1 which is 5-isobutylsulfonyl-1,3,4-thiadiazole-2-carbonitrile.

75. The compound as defined in claim 1 which is 5-propylsulfonyl-1,3,4-thiadiazole-2-carboxylic acid hexylamide.

76. The compound as defined in claim 1 which is 5-isopropylsulfonyl-1,3,4-thiadiazole-2-carboxylic acid cyclohexylmethylamide.

77. The compound as defined in claim 1 which is 5-isopropylsulfinyl-1,3,4-thiadiazole-2-carboxylic acid cyclohexylmethylamide.

78. The compound as defined in claim 1 which is 5-propylsulfinyl-1,3,4-thiadiazole-2-carboxylic acid butylamide.

79. The compound as defined in claim 1 which is 5-propylsulfinyl-1,3,4-thiadiazole-2-carboxylic acid sec.-butylamide.

80. The compound as defined in claim 1 which is 5-propylsulfinyl-1,3,4-thiadiazole-2-carboxylic acid hexylamide.

81. The compound as defined in claim 1 which is 5-propylsulfinyl-1,3,4-thiadiazole-2-carboxylic acid dimethylamide.

82. The compound as defined in claim 1 which is 5-methylsulfinyl-1,3,4-thiadiazole-2-carbonitrile.

83. The compound as defined in claim 1 which is 5-methylsulfinyl-1,3,4-thiadiazole-2-carboxyamide.

84. The compound as defined in claim 1 which is 5-isopropylsulfinyl-1,3,4-thiadiazole-2-carboxamide.

85. The compound as defined in claim 1 which is 5-isopropylsulfinyl-1,3,4-thiadiazole-2-carbonitrile.

86. The compound as defined in claim 1 which is 5-pentylsulfonyl-1,3,4-thiadiazole-2-carboxylic acid ethylester.

87. The compound as defined in claim 1 which is 5-pentylsulfonyl-1,3,4-thiadiazole-2-carbonitrile.

88. The compound as defined in claim 1 which is 5-hexylsulfonyl-1,3,4-thiadiazole-2-carbonitrile.

89. The compound as defined in claim 1 which is 5-pentylsulfonyl-1,3,4-thiadiazole-2-carboxamide.

90. The compound as defined in claim 1 which is 5-hexylsulfonyl-1,3,4-thiadiazole-2-carboxamide.

91. The compound as defined in claim 2 which is 5-propylsulfonyl-1,3,4-thiadiazole-2-carboxylic acid N,N-trimethyleneamide.

92. The compound as defined in claim 2 which is 5-butylsulfonyl-1,3,4-thiadiazole-2-carboxylic acid N,N-trimethyleneamide.

93. The compound as defined in claim 1 which is 5-butylsulfinyl-1,3,4-thiadiazole-2-carbonitrile.

94. The compound as defined in claim 2 which is 5-ethylsulfonyl-1,3,4-thiadiazole-2-carboxylic acid N,N-trimethyleneamide.

95. The compound as defined in claim 1 which is 5-isopropylsulfonyl-1,3,4-thiadiazole-2-carboxylic acid methylamide.

96. The compound as defined in claim 1 which is 5-isopropylsulfonyl-1,3,4-thiadiazole-2-carboxylic acid ethylamide.

97. The compound as defined in claim 1 which is 5-isopropylsulfonyl-1,3,4-thiadiazole-2-carboxylic acid isopropylamide.

98. The compound as defined in claim 1 which is 5-isopropylsulfonyl-1,3,4-thiadiazole-2-carboxylic acid propylamide.

99. The compound as defined in claim 1 which is 5-isopropylsulfonyl-1,3,4-thiadiazole-2-carboxylic acid butylamide.

100. The compound as defined in claim 1 which is 5-isopropylsulfonyl-1,3,4-thiadiazole-2-carboxylic acid isobutylamide.

101. The compound as defined in claim 1 which is 5-isopropylsulfonyl-1,3,4-thiadiazole-2-carboxylic acid sec.-butylamide.

102. The compound as defined in claim 1 which is 5-isopropylsulfinyl-1,3,4-thiadiazole-2-carboxylic acid methylamide.

103. The compound as defined in claim 1 which is 5-isopropylsulfinyl-1,3,4-thiadiazole-2-carboxylic acid ethylamide.

104. The compound as defined in claim 1 which is 5-(2-propenylsulfinyl)-1,3,4-thiadiazole-2-carboxylic acid methylamide.

105. The compound as defined in claim 1 which is 5-methylsulfonyl-1,3,4-thiadiazole-2-carboxylic acid N-ethyl-N-butylamide.

106. The compound as defined in claim 1 which is 5-isopropylsulfinyl-1,3,4-thiadiazole-2-carboxylic acid propylamide.

107. The compound as defined in claim 1 which is 5-isopropylsulfonyl-1,3,4-thiadiazole-2-carboxylic acid isopropylamide.

108. The compound as defined in claim 1 which is 5-isopropylsulfonyl-1,3,4-thiadiazole-2-carboxylic acid dimethylamide.

109. The compound as defined in claim 1 which is 5-butylsulfonyl-1,3,4-thiadiazole-2-carboxylic acid methylamide.

110. The compound as defined in claim 1 which is 5-butylsulfonyl-1,3,4-thiadiazole-2-carboxylic acid ethylamide.

111. The compound as defined in claim 1 which is 5-butylsulfonyl-1,3,4-thiadiazole-2-carboxylic acid propylamide.

112. The compound as defined in claim 1 which is 5-butylsulfonyl-1,3,4-thiadiazole-2-carboxylic acid (2-methoxyethyl)-amide.

113. The compound as defined in claim 1 which is 5-butylsulfonyl-1,3,4-thiadiazole-2-carboxylic acid isopropylamide.

114. The compound as defined in claim 1 which is 5-butylsulfinyl-1,3,4-thiadiazole-2-carboxylic acid methylamide.

115. The compound as defined in claim 1 which is 5-butylsulfinyl-1,3,4-thiadiazole-2-carboxylic acid ethylamide.

116. The compound as defined in claim 1 which is 5-butylsulfinyl-1,3,4-thiadiazole-2-carboxylic acid propylamide.

117. The compound as defined in claim 1 which is 5-butylsulfinyl-1,3,4-thiadiazole-2-carboxylic acid (2-methoxyethyl)-amide.

118. The compound as defined in claim 1 which is 5-butylsulfinyl-1,3,4-thiadiazole-2-carboxylic acid isopropylamide.

119. The compound as defined in claim 1 which is 5-methylsulfonyl-1,3,4-thiadiazole-2-carboxylic acid N-butyl-N-methylamide.

120. The compound as defined in claim 1 which is 5-methylsulfonyl-1,3,4-thiadiazole-2-carboxylic acid N-isobutyl-N-methylamide.

121. The compound as defined in claim 1 which is 5-methylsulfonyl-1,3,4-thiadiazole-2-carboxylic acid N,N-diethylamide.

122. The compound as defined in claim 1 which is 5-sec.-butylsulfonyl-1,3,4-thiadiazole-2-carboxylic acid methylamide.

123. The compound as defined in claim 1 which is 5-sec.-butylsulfonyl-1,3,4-thiadiazole-2-carboxylic acid ethylamide.

124. The compound as defined in claim 1 which is 5-cyclohexylsulfonyl-1,3,4-thiadiazole-2-carboxamide.

125. The compound as defined in claim 1 which is 5-cyclohexylsulfonyl-1,3,4-thiadiazole-2-carbonitrile.

126. The compound as defined in claim 1 which is 5-methylsulfonyl-1,3,4-thiadiazole-2-carboxylic acid N,N-dipropylamide.

127. The compound as defined in claim 1 which is 5-sec. butylsulfonyl-1,3,4-thiadiazole-2-carboxylic acid cyclopropylamide.

128. The compound as defined in claim 1 which is 5-pentylsulfinyl-1,3,4-thiadiazole-2-carbonitrile.

129. The compound as defined in claim 1 which is 5-hexylsulfinyl-1,3,4-thiadiazole-2-carbonitrile.

130. The compound as defined in claim 1 which is 5-pentylsulfonyl-1,3,4-thiadiazole-2-carboxylic acid methylamide.

131. The compound as defined in claim 1 which is 5-hexylsulfonyl-1,3,4-thiadiazole-2-carboxylic acid methylamide.

132. The compound as defined in claim 1 which is 5-cyclohexylsulfinyl-1,3,4-thiadiazole-2-carbonitrile.

133. The compound as defined in claim 1 which is 5-sec. butylsulfonyl-1,3,4-thiadiazole-2-carboxylic acid (2-methoxyethyl)-amide.

134. The compound as defined in claim 1 which is 5-sec.-butylsulfinyl-1,3,4-thiadiazole-2-carboxylic acid methylamide.

135. The compound as defined in claim 1 which is 5-sec.-butylsulfinyl-1,3,4-thiadiazole-2-carboxylic acid ethylamide.

136. The compound as defined in claim 1 which is 5-pentylsulfonyl-1,3,4-thiadiazole-2-carboxylic acid ethylamide.

137. The compound as defined in claim 1 which is 5-hexylsulfonyl-1,3,4-thiadiazole-2-carboxylic acid ethylamide.

138. The compound as defined in claim 1 which is 5-pentylsulfinyl-1,3,4-thiadiazole-2-carboxylic acid ethylamide.

139. The compound as defined in claim 1 which is 5-hexylsulfinyl-1,3,4-thiadiazole-2-carboxylic acid ethylamide.

140. The compound as defined in claim 1 which is 5-methylsulfinyl-1,3,4-thiadiazole-2-carboxylic acid N,N-diethylamide.

141. The compound as defined in claim 1 which is 5-sec.-butylsulfonyl-1,3,4-thiadiazole-2-carboxylic acid isopropylamide.

142. The compound as defined in claim 1 which is 5-sec. butylsulfinyl-1,3,4-thiadiazole-2-carboxylic acid cyclopropylamide.

143. The compound as defined in claim 1 which is 5-pentylsulfonyl-1,3,4-thiadiazole-2-carboxylic acid propylamide.

144. The compound as defined in claim 1 which is 5-pentylsulfonyl-1,3,4-thiadiazole-2-carboxylic acid isopropylamide.

145. The compound as defined in claim 1 which is 5-pentylsulfonyl-1,3,4-thiadiazole-2-carboxylic acid cyclopropylamide.

146. The compound as defined in claim 1 which is 5-pentylsulfonyl-1,3,4-thiadiazole-2-carboxylic acid butylamide.

147. The compound as defined in claim 1 which is 5-pentylsulfonyl-1,3,4-thiadiazole-2-carboxylic acid sec.-butylamide.

148. The compound as defined in claim 1 which is 5-pentylsulfonyl-1,3,4-thiadiazole-2-carboxylic acid isobutylamide.

149. The compound as defined in claim 1 which is 5-pentylsulfinyl-1,3,4-thiadiazole-2-carboxylic acid propylamide.

150. The compound as defined in claim 1 which is 5-pentylsulfinyl-1,3,4-thiadiazole-2-carboxylic acid isopropylamide.

151. The compound as defined in claim 2 which is 5-pentylsulfinyl-1,3,4-thiadiazole-2-carboxylic acid allylamide.

152. The compound as defined in claim 1 which is 5-pentylsulfinyl-1,3,4-thiadiazole-2-carboxylic acid cyclopropylamide.

153. The compound as defined in claim 1 which is 5-pentylsulfinyl-1,3,4-thiadiazole-2-carboxylic acid butylamide.

154. The compound as defined in claim 1 which is 5-pentylsulfinyl-1,3,4-thiadiazole-2-carboxylic acid sec.-butylamide.

155. The compound as defined in claim 1 which is 5-pentylsulfinyl-1,3,4-thiadiazole-2-carboxylic acid isobutylamide.

156. The compound as defined in claim 1 which is 5-cyclopentylsulfonyl-1,3,4-thiadiazole-2-carboxylic acid methylamide.

157. The compound as defined in claim 1 which is 5-cyclopentylsulfonyl-1,3,4-thiadiazole-2-carboxylic acid ethylamide.

158. The compound as defined in claim 1 which is 5-sec.-butylsulfinyl-1,3,4-thiadiazole-2-carboxylic acid (2-methoxyethyl)-amide.

159. The compound as defined in claim 1 which is 5-sec.-butylsulfonyl-1,3,4-thiadiazole-2-carboxylic acid (3-methoxypropyl)-amide.

160. The compound as defined in claim 1 which is 5-cyclopentylsulfonyl-1,3,4-thiadiazole-2-carboxylic acid propylamide.

161. The compound as defined in claim 1 which is 5-cyclopentylsulfonyl-1,3,4-thiadiazole-2-carboxylic acid isopropylamide.

162. The compound as defined in claim 1 which is 5-cyclopentylsulfonyl-1,3,4-thiadiazole-2-carboxylic acid cyclopropylamide.

163. The compound as defined in claim 1 which is 5-cyclopentylsulfonyl-1,3,4-thiadiazole-2-carboxylic acid butylamide.

164. The compound as defined in claim 1 which is 5-cyclopentylsulfonyl-1,3,4-thiadiazole-2-carboxylic acid dimethylamide.

165. The compound as defined in claim 1 which is 5-pentylsulfonyl-1,3,4-thiadiazole-2-carboxylic acid dimethylamide.

166. The compound as defined in claim 1 which is 5-pentylsulfonyl-1,3,4-thiadiazole-2-carboxylic acid (3-methoxypropyl)-amide.

167. The compound as defined in claim 1 which is 5-hexylsulfonyl-1,3,4-thiadiazole-2-carboxylic acid propylamide.

168. The compound as defined in claim 1 which is 5-hexylsulfonyl-1,3,4-thiadiazole-2-carboxylic acid isopropylamide.

169. The compound as defined in claim 1 which is 5-hexylsulfonyl-1,3,4-thiadiazole-2-carboxylic acid (2-methoxyethyl)-amide.

170. The compound as defined in claim 1 which is 5-hexylsulfonyl-1,3,4-thiadiazole-2-carboxylic acid (3-methoxypropyl)-amide.

171. The compound as defined in claim 1 which is 5-cyclopentylsulfinyl-1,3,4-thiadiazole-2-carboxylic acid methylamide.

172. The compound as defined in claim 1 which is 5-cyclopentylsulfinyl-1,3,4-thiadiazole-2-carboxylic acid ethylamide.

173. The compound as defined in claim 1 which is 5-methylsulfonyl-1,3,4-thiadiazole-2-carboxylic acid N,N-diisopropylamide.

174. The compound as defined in claim 1 which is 5-sec.-butylsulfinyl-1,3,4-thiadiazole-2-carboxylic acid (3-methoxypropyl)-amide.

175. The compound as defined in claim 1 which is 5-hexylsulfinyl-1,3,4-thiadiazole-2-carboxylic acid propylamide.

176. The compound as defined in claim 1 which is 5-hexylsulfinyl-1,3,4-thiadiazole-2-carboxylic acid isopropylamide.

177. The compound as defined in claim 1 which is 5-hexylsulfinyl-1,3,4-thiadiazole-2-carboxylic acid (2-propenyl)-amide.

178. The compound as defined in claim 1 which is 5-hexylsulfinyl-1,3,4-thiadiazole-2-carboxylic acid cyclopropylamide.

179. The compound as defined in claim 1 which is 5-hexylsulfinyl-1,3,4-thiadiazole-2-carboxylic acid (2-methoxyethyl)-amide.

180. The compound as defined in claim 1 which is 5-hexylsulfonyl-1,3,4-thiadiazole-2-carboxylic acid cyclopropylamide.

181. The compound as defined in claim 1 which is 5-hexylsulfinyl-1,3,4-thiadiazole-2-carboxylic acid (3-methoxypropyl)-amide.

182. The compound as defined in claim 1 which is 5-ethylsulfonyl-1,3,4-thiadiazole-2-carboxylic acid ethylamide.

* * * * *